(12) United States Patent
Iyer et al.

(10) Patent No.: US 12,156,799 B2
(45) Date of Patent: Dec. 3, 2024

(54) DEVICE AND METHOD FOR PREVENTING STENOSIS AT AN ANASTOMOSIS SITE

(71) Applicant: VASCULAR THERAPIES, INC., Cresskill, NJ (US)

(72) Inventors: Sriram Iyer, New York, NY (US); Gerald Dorros, Wilson, WY (US)

(73) Assignee: Vascular Therapies, Inc., Cresskill, NJ (US)

( * ) Notice: Subject to any disclaimer, the term of this patent is extended or adjusted under 35 U.S.C. 154(b) by 654 days.

(21) Appl. No.: 16/983,893

(22) Filed: Aug. 3, 2020

(65) Prior Publication Data
US 2020/0360126 A1 Nov. 19, 2020

Related U.S. Application Data

(63) Continuation of application No. 15/284,234, filed on Oct. 3, 2016, now abandoned, which is a continuation
(Continued)

(51) Int. Cl.
*A61F 2/06* (2013.01)
*A61F 2/82* (2013.01)
(Continued)

(52) U.S. Cl.
CPC ............... *A61F 2/064* (2013.01); *A61F 2/82* (2013.01); *A61F 2/844* (2013.01); *A61F 2/856* (2013.01);
(Continued)

(58) Field of Classification Search
CPC .......... A61F 2/064; A61F 2/844; A61F 2/962; A61F 2/82; A61F 2/90; A61F 2/856; A61F 2/954; A61F 2210/0004; A61F 2230/0041; A61F 2230/0043; A61F 2/966; A61F 2/852; A61F 2250/0067; A61F 2250/006; A61F 2002/821; A61L 31/125; A61L 31/16;
(Continued)

(56) References Cited

U.S. PATENT DOCUMENTS 7,108,701 B2* 9/2006 Evens ..................... A61P 37/06
606/155
2002/0052572 A1* 5/2002 Franco .................... A61L 31/06
604/8
(Continued)

*Primary Examiner* — William H Matthews
(74) *Attorney, Agent, or Firm* — Mayer Brown LLP

(57) ABSTRACT

The present invention relates to treating or preventing stenosis at an anastomosis site. In one embodiment, the present invention is a stent is curved along the longitudinal axis for placement in and adjacent to the graft orifice. In a further embodiment, the stent is drug coated to allow delivery of antivasculoproliferative drugs directly to the vicinity of the graft orifice. In a further embodiment, the stent is expandable by use of an external wire. In another embodiment, the present invention is a kit comprising the specially configured stent together with a sleeve comprising a biocompatible matrix material and a pharmaceutical agent, wherein the sleeve is applied to the external surface of the vessel or graft, resulting in extravascular delivery of a pharmaceutical agent. Methods for treating or preventing stenosis at an anastomosis site by applying the extravascular sleeve and the intravascular stent are also provided.

47 Claims, 11 Drawing Sheets

Related U.S. Application Data of application No. 13/850,450, filed on Mar. 26, 2013, now abandoned, which is a continuation of application No. 13/015,571, filed on Jan. 27, 2011, now abandoned.

(60) Provisional application No. 61/298,631, filed on Jan. 27, 2010.

(51) Int. Cl.
*A61F 2/844* (2013.01)
*A61F 2/856* (2013.01)
*A61F 2/90* (2013.01)
*A61F 2/954* (2013.01)
*A61K 31/436* (2006.01)
*A61L 27/54* (2006.01)
*A61L 31/12* (2006.01)
*A61L 31/16* (2006.01)
*A61F 2/852* (2013.01)
*A61F 2/966* (2013.01)

(52) U.S. Cl.
CPC ............... *A61F 2/90* (2013.01); *A61F 2/954* (2013.01); *A61K 31/436* (2013.01); *A61L 27/54* (2013.01); *A61L 31/125* (2013.01); *A61L 31/16* (2013.01); *A61F 2002/821* (2013.01); *A61F 2/852* (2013.01); *A61F 2/966* (2013.01); *A61F 2210/0004* (2013.01); *A61F 2230/0041* (2013.01); *A61F 2230/0043* (2013.01); *A61F 2250/006* (2013.01); *A61F 2250/0067* (2013.01); *A61L 2300/204* (2013.01)

(58) Field of Classification Search
CPC .. A61L 27/54; A61L 2300/204; A61K 31/436
See application file for complete search history.

(56) References Cited

U.S. PATENT DOCUMENTS

2005/0004158 A1* 1/2005 Iyer ................. A61B 17/0057
514/291
2009/0182409 A1* 7/2009 Feld ..................... A61F 2/856
623/1.2

* cited by examiner

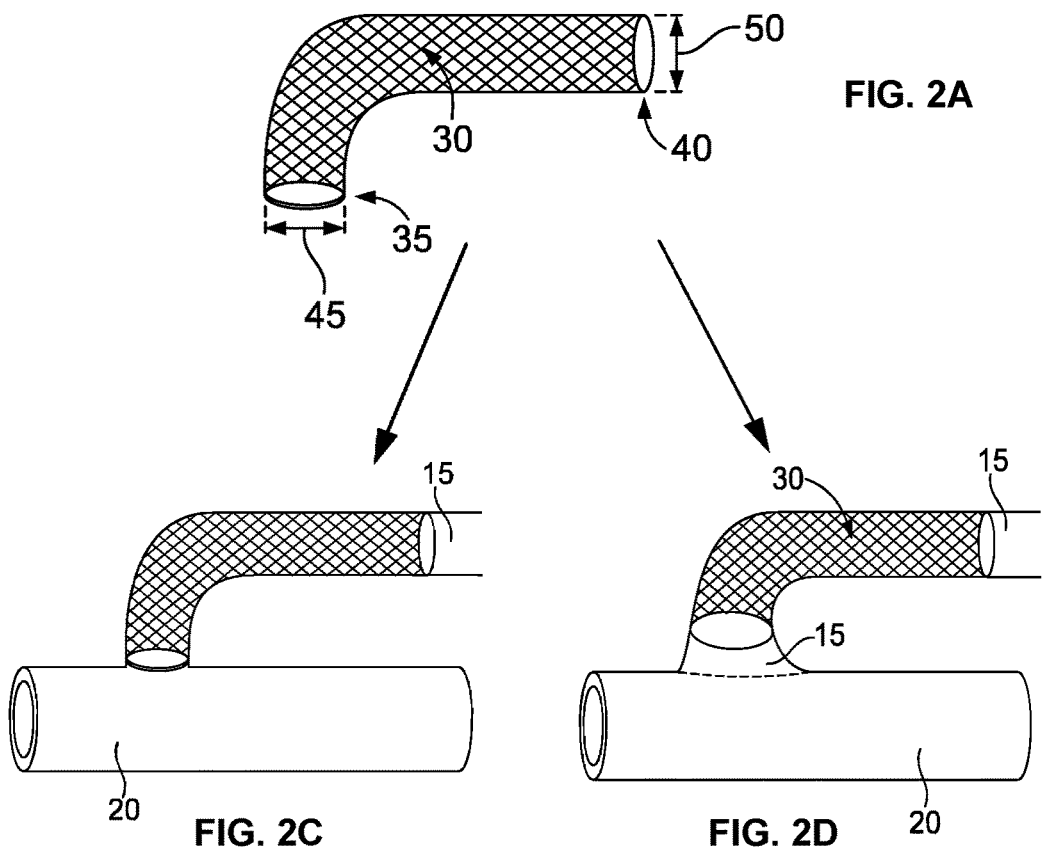
FIG. 2A
FIG. 2C
FIG. 2D
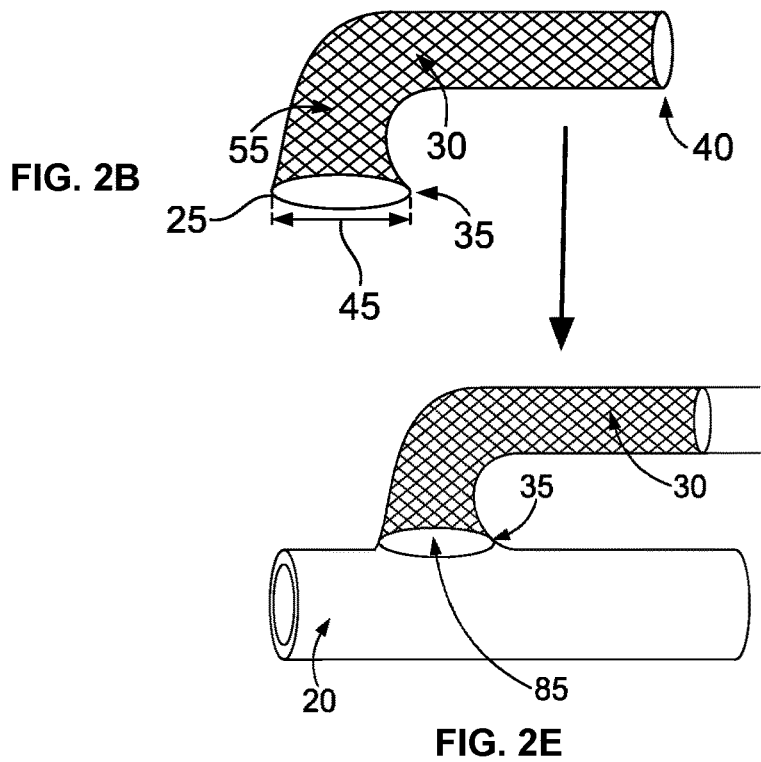
FIG. 2B
FIG. 2E

9S003 (AV Graft + Stent)
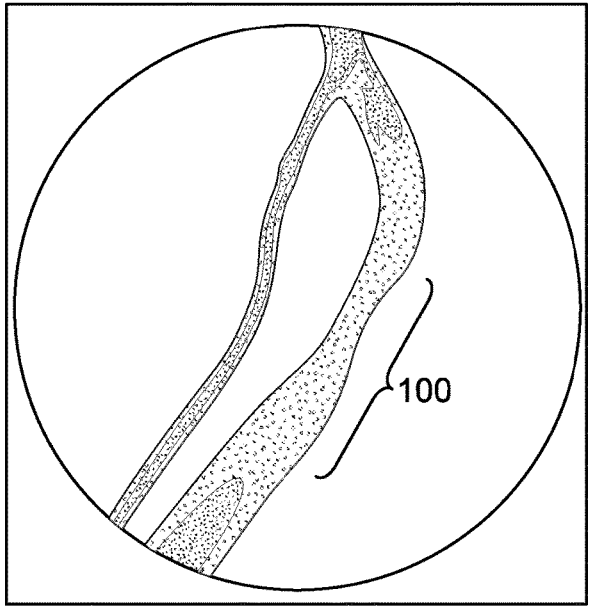
FIG. 12A
9S004 (AV Graft + Stent)
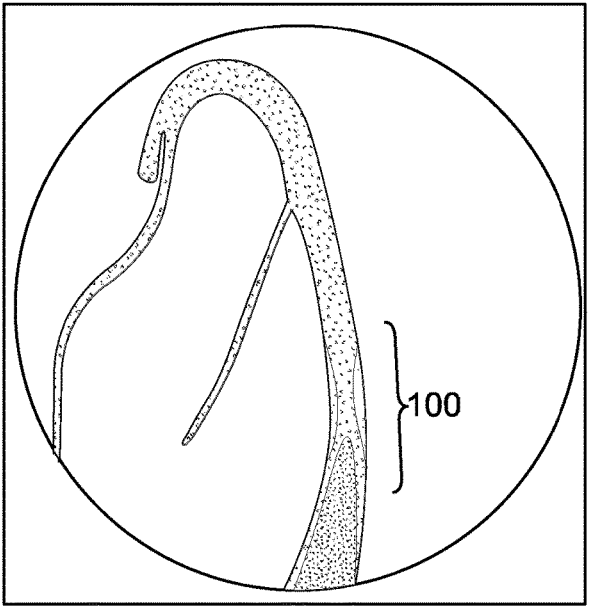
FIG. 12B
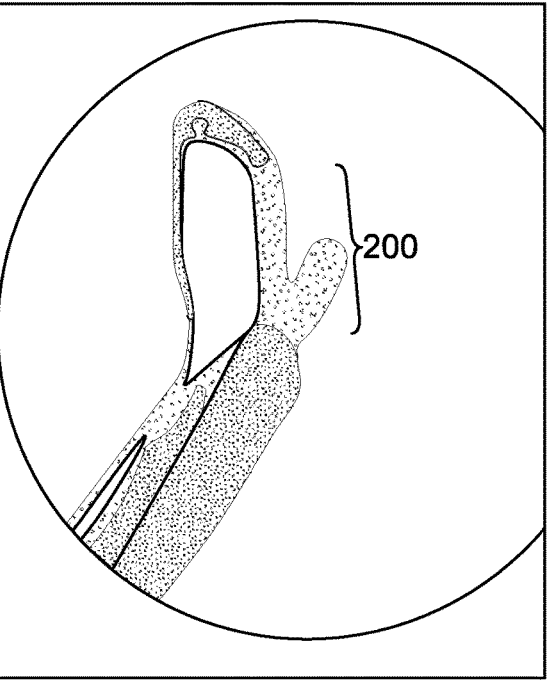
9S014 (AV Graft + Stent+Sirolimus Eluting Collagen Matrix)
FIG. 12C
9S015 (AV Graft + Stent+Sirolimus Eluting Collagen Matrix)
FIG. 12D

9S003 (AV Graft + Stent)

9S004 (AV Graft + Stent)

9S014 (AV Graft + Stent+Sirolimus Eluting Collagen Matrix)

9S015 (AV Graft + Stent+Sirolimus Eluting Collagen Matrix)

9S005 (Left Control AV Fistula)

9S005 (Right Control AV Fistula)

9S019 (Left AV Fistula)

9S019 (Right AV Fistula)

9S005 (Left Control AV Fistula)

9S005 (Right Control AV Fistula)

9S019 (Left AV Fistula - day 28)

9S019 (Left AV Fistula - day 62)

FIG. 16D  Expanded version of FIG. 16 C

DEVICE AND METHOD FOR PREVENTING STENOSIS AT AN ANASTOMOSIS SITE

CROSS-REFERENCE TO RELATED APPLICATIONS

This application is a continuation of U.S. patent application Ser. No. 15/284,234, filed on Oct. 3, 2016, which is a continuation of U.S. patent application Ser. No. 13/850,450, filed Mar. 26, 2013, which is a continuation of U.S. patent application Ser. No. 13/015,571, filed Jan. 27, 2011 and abandoned on Mar. 29, 2013, which claims priority to U.S. Provisional Patent Application No. 61/298,631 filed Jan. 27, 2010.

FIELD

The present invention relates generally to therapeutic implants, devices, and methods useful for preventing, suppressing, or treating stenosis(es) at and around the site of an anastomosis. The invention also relates to stents specifically configured for placement at an anastomosis or a fistula, and methods for combining those sites with extravascular therapeutic implants comprising a matrix material and a therapeutic agent. The specifically configured stents are also useful for treatment of stenosis or narrowings remote from an anastomosis, e.g., treatment of an ostial stenosis in a side branch, treatment of a stenosis in a central vein (e.g. cephalic arch) and the like.

BACKGROUND

Vascular procedures such as construction of arterio-venous grafts and arterio-venous fistulae are performed to provide vascular access to facilitate hemodialysis in patients with end stage renal disease. Interventions like angioplasty are performed to treat, for example, narrowing (stenosis) or occlusion resulting from vasculoproliferative conditions such as obstructive intimal hyperplasia or atherosclerosis. Vascular access for hemodialysis can be constructed as an arterio-venous fistula (AVF) (e.g., Brecisa-Cimino), or as a graft (AVG) interposing prosthetic material (e.g., polytetrafluoroehtylene, "PTFE") between an artery and a vein. During the construction of an AV fistula, a vein is joined or attached to an artery to enable direct communication between the arterial and venous lumen. In one method for creating an arterio-venous fistula, a vein in the forearm, arm or thigh is joined or attached to an adjacent artery so that there is a direct communication between the arterial and venous lumen. During the construction of an AV fistula, the severed end of the vein is dislodged from its natural location and the vein curved along its longitudinal axis so that the vein may be connected directly to the artery. The site(s) of vascular union, e.g. artery and vein or graft and artery or graft and vein are referred to as the vascular anastomotic(s) site or vascular anastomosis. The anastomosis can be completed using sutures or clips, or with the help of devices specially designed for creation and completion of such anastomosis. The graft can be made of synthetic materials, like polytetrafluoroethylene (PTFE) for example, or can be comprised of autologous tissue (e.g. saphenous vein, mammary artery, etc.).

Subsequent to the construction of a fistula or graft, the anastomotic site connecting the artery and the vein (e.g. in case of a fistula) and the graft/artery and the graft/venous anastomotic sites (e.g. in case of AV graft) undergo healing. However, a certain proportion of these vascular access and vascular graft surgeries fail as a result of narrowing or stenosis at and around the anastomotic sites. As many as 60 percent of AV fistulae do not develop ("failure to mature") into a vascular access suitable to support dialysis; an important reason for this maturation failure is luminal narrowing, or an obstructive stenosis, at and around the venous end, commonly referred to as a Juxta Anastomotic Stenosis (JAS). Stenosis can also occur at sites remote from the anastomosis (e.g. cephalic arch stenosis, stenosis at the site of needle punctures, etc). In the case of AV grafts, the anastomotic site of the PTFE graft and the vein often develop a stenosis resulting in slow flow and thrombosis of the graft making it unusable as a vascular access for dialysis. Similar lesions develop in grafts placed in the arterial circulation, (e.g. peripheral arterial bypass using prosthetic PTFE grafts or coronary artery or peripheral artery bypass using biological tissue conduits like saphenous vein). Failure or dysfunction of grafts used in coronary artery bypass graft surgery as well as peripheral vascular surgery (e.g., aorta-iliac, femoral-femoral, femoral-popliteal, femoral-tibial, etc.) are also well known. In general, stenosis in grafts used to bypass pathology in the arterial system develops at a slower rate when compared to the failure of hemodialysis access grafts or fistulae described above.

An important cause of failure of vascular grafts is usually related to luminal narrowing of the vessel or prosthetic conduit, at or around the vascular anastomotic site(s). One reason for this narrowing is a consequence of a vasculoproliferative response and frequently results in graft thrombosis and fistula failure. Other pathologies can also affect the performance of a graft or fistula, e.g. infection, pseudo-aneurysm, bleeding etc. Although the discussion above has focused on anastomosis involving blood vessels (vascular anastomosis), other examples of anastomosis, which in broad terms includes the site or region of union of two hollow tubes or conduits include: anastomosis involving the ureter, trachea/bronchi, fallopian tubes, segments of bowel, etc., and problems of luminal narrowing can also be seen at and around these anastomotic sites. The methods and devices described in this application are intended for use in both vascular as well as these non-vascular applications.

Neointimal hyperplasia, a manifestation of the vasculoproliferative response, affects the anastomotic orifice and adjacent vessel. The vessel wall thickens and the lumen narrows often due to migration and proliferation of smooth muscle cells. Left untreated, stenosis eventually leads to occlusion and graft or fistula failure. The etiology of graft and fistula failures may relate to a variety of physical stimuli (e.g., shear stress causing hemodynamic disturbances such as increased resistance from a non-dilated vein, turbulent flow replacing laminar flow), chemical stimuli, or biological stimuli, as well as infection or foreign body rejection. For example, in an arterio-venous fistula, dislodging the vein from its natural location can cause stress and injury, which can lead to an increased risk of stenosis. As stenosis in the graft or fistula becomes progressively more severe, the graft or fistula becomes dysfunctional and access for medical procedures becomes suboptimal or absent, and precludes use of that vascular access to perform hemodialysis. Diminished blood flow in grafts connecting two arteries (e.g. grafts used for coronary artery bypass graft surgery or peripheral arterial bypass surgery) leads to problems related to diminished or lack of blood supply (ischemia) to the organ supplied by the bypassed artery.

Once the stenosis has occurred, one of the treatment options involves reduction or obliteration of the narrowing and restoration of blood flow through the graft (thereby permitting resumption of adequate hemodialysis) by means of non-surgical, percutaneous catheter-based treatments such as balloon angioplasty. Balloon angioplasty, in one aspect, involves deployment of a balloon catheter at the site of the blockage, and inflating the balloon to increase the minimum luminal diameter (MLD) of the vessel by compressing the material causing the restriction against the interior of the vessel wall. Depending on the length, severity and characteristics of the restriction (e.g. degree of stenosis resulting in the blood flow restriction, and amount of calcification) the balloon may have to be repositioned and inflated and deflated more than once in order to attain optimal lumen expansion. When completed, the balloon catheter is withdrawn from the system.

Although balloon angioplasty can be used as a "stand alone" procedure, it is frequently accompanied by deployment of a stent. As is known in the art, a stent is an expandable scaffolding or support device which is placed within the vasculature (endovascular implant). Following angioplasty, mechanical (elastic) recoil and negative vascular remodeling can be important contributors to re-narrowing (restenosis) at the site of the original restrictions. An endovascular stent is effective in countering recoil and also very effective in preventing a dissection flap, which can result following balloon angioplasty of the restriction or stenosis, from falling back into the vascular lumen. Such a dissection flap has the potential to completely obstruct blood flow soon after angioplasty, resulting in acute vessel closure. The stent is very effective in preventing acute closure. The stents known in the prior art are either "balloon expandable" or "self expanding," and when deployed endovascularly, the stent after expansion abuts directly against the inner lining of the vessel wall (intimal surface). Balloon-expandable stents are disclosed in U.S. Pat. No. 4,733,665 to Palmaz. Self-expanding stents are disclosed in U.S. Pat. No. 5,443,500 to Sigwart, U.S. Pat. No. 4,655,771 to Wallsten, U.S. Pat. No. 5,061,275 to Wallsten et al., and U.S. Pat. No. 5,645,559 to Hachtman et al. Despite using a plain stent (i.e. bare metal, partially or completely biodegradable, non-drug-coated stent) following angioplasty, this form of treatment (endovascular stent placement) has an important risk of failure, i.e., the risk of re-narrowing (restenosis) or occlusion at the treatment site. In other words, the scaffolding effect of the bare metal stent by itself, cannot completely overcome the problem of restenosis at the treatment site. The use of drug eluting stents in vascular procedures to overcome or reduce the problem of restenosis is also well known to those skilled in the art. Drug eluting stents are, for example, disclosed generally in U.S. Pat. No. 5,545,208 to Wolff, U.S. Pat. No. 6,899,731 to Li et al., U.S. Pat. No. 6,273,913 to Wright et al., and U.S. Pat. Pub. No. 2009/0182404 to Shookoohi.

Unless stenosis(es) at the treatment sites (e.g. at and around the site of vascular anastomosis) can be effectively treated, graft or fistula failure tends to follow. In the event of hemodialysis AV graft or fistula failure, the patient has to undergo an immediate/urgent endovascular procedure (i.e., a non-surgical, catheter-based percutaneous procedure such as a thrombectomy) to "declot (remove the thrombus within)" or undergo repeat vascular surgery to place another vascular access, which could be another graft or fistula, at a different site, or undergo placement of a catheter, unless the patient receives a kidney transplant. Given the obvious problems of repeat procedures and surgery (e.g. mortality, morbidity, cost, prolonged hospitalizations, infections, etc.), and the limited availability of transplants, there is a need for a treatment that is both effective and long lasting (i.e. durable) in the prevention and treatment of dialysis vascular access and graft anastomotic stenosis.

The configurations of traditional stents have limitations for treating stenosis at and adjacent to an anastomosis site of fistula and grafts. Adjacent to the anastomotic orifice of an arterio-venous fistula or graft, the vein or graft protrudes from the artery or blood vessel at an angle, curving along its longitudinal axis toward its origin in the body ("candy cane configuration"). (FIGS. 1-3). Because currently available stents are not curved along the longitudinal axis, they are not well suited for placement at and adjacent to the anastomotic site of a fistula or graft because they cannot extend into the curvature of the blood vessel. In addition, these stents cannot be easily maneuvered through the graft orifice and into the artery at an arterio-venous fistula because of the angulation, U-turn or hairpin configuration of the vessels at the anastomotic site.

Yet another limitation of currently available stents relates to the configuration at the anastomosis. Two blood vessels, or a graft and a blood vessel, can be joined at a right angle (see FIG. 1A). If the anastomosis is at a right angle, the edge of a cylindrical stent can be positioned such that the stent edge can be aligned and lined up to match the edge of the blood vessel at the right angle anastomosis (see FIG. 1B). However, in most instances, the operator bevels the edge of the blood vessel prior to creating the anastomosis (see FIG. 1C). In this case, it can be appreciated that a cylindrical stent edge cannot be exactly lined up against the edge of the beveled blood vessel. Either the stent will be a "little short" of the anastomosis (see FIG. 2D, 16A) or it will protrude across the anastomosis into the other vessel (see FIG. 16B). Accordingly, there is a need for a stent that will address both undesirable conditions related to the placement of a stent having a square-cut, right angled end/edge at the site of an anastomosis where the vessels of the anastomosis are not perpendicular to each other.

The diameter of the two blood vessels that are being joined at the anastomosis may be different; similarly the diameter of the blood vessel at the level of the anastomosis and the diameter at a point away from the anastomosis may be different. Hence, the stents used herein may need to be tapered. The term tapered indicates that the diameter of the expanded stent at one end differs when compared to the diameter of the expanded stent at the opposite end. This difference in diameter may occur gradually over the length of the stent or it may occur abruptly at some point along the length of the stent.

Another known method for treating and preventing stenosis is the implantation of a prosthetic device, or "sleeve" on the outer surface of the vessel or graft which then elutes antivasculoproliferative drugs or agents such as rapamycin (sirolimus), paclitaxel, tacrolimus, everolimus, zotarolimus and other cell cycle inhibitors or similarly-functioning agents. Such a sleeve is disclosed in U.S. Pat. No. 6,726,933, entitled "Apparatus and Methods for Preventing or Treating Failure of Hemodialysis Vascular Access and Other Vascular Grafts," and co-pending U.S. Patent Application Publication No. 2005/0004158, entitled "Medical Implants and Methods For Regulating the Tissue Response to Vascular Closure Devices," filed on Jun. 18, 2004.

There is therefore a need for a stent that can be used together with the above-described wrap or sleeve to prevent, suppress or treat stenosis at and around an anastomosis site or fistula. And there is a need for methods for combining such extravascular therapeutic implants comprising a matrix material together with an endovascular stent implant. There is also a need to combine a traditional self expanding nitinol stent or a balloon expandable stent together with a perivascular drug eluting sleeve. Any of the stents described herein can be used in combination with a perivascular wrap in order to prevent, suppress, or treat stenosis. (See FIGS. 18 and 19).

SUMMARY

In one embodiment, the present invention is a stent that is specially configured for placement at an anastomosis site in that the stent is curved along the longitudinal axis for placement at and/or adjacent to the anastomosis. Such a stent can also be used away from an anastamosis site; for example, at a curved part of a vessel remote from the anastomosis, or at the bifurcation of a vessel. In another embodiment, the stent is specially configured for placement at an anastomosis site in that the stent is beveled, flared or trumpeted at the edge to facilitate deployment at the anastomosis. In another embodiment the stent is tapered so that the diameter at one end of the expanded stent is different from the other end. In another embodiment the stent is coated with a polymer like PTFE; the coating may extend along the entire length and circumference of the stent or it may partially cover the stent. In a further embodiment, the stent is drug coated to allow local delivery of anti-vasculo-proliferative drugs directly to the vicinity at and around the site of anastomosis. In a further embodiment a combination of a drug eluting balloon expandable stent and a self expandable is used; the balloon expandable drug eluting stent is sandwiched between the self expanding stent and the vessel wall. In a further embodiment, a wire or wire like delivery system with a handle is attached to the exterior surface of the stent in its compacted state, wherein manipulating the wire or another release mechanism pulls the exterior surface of the stent toward the interior surface of the vessel, resulting in expansion and deployment of the stent.

In another embodiment, a combination of a balloon expandable drug eluting stent and a non drug coated self expanding stent is used. In this case, the balloon expandable drug eluting stent is first deployed at and around the anastomosis of an AV fistula or graft. The self expanding nitinol stent is then deployed such that the balloon expandable drug eluting stent is sandwiched between the expanded self expanding nitinol stent and the inner lining of the graft and/or the inner wall of the blood vessel. The balloon expandable drug eluting stent can be made of a biodegradable material or a biostable material like stainless steel or cobalt chromium.

In another embodiment, the balloon expandable or self expandable stent may be partially or completely covered by a polymer, fabric or biological coating. An example of such a covering that may be used for the stent is polytetrafluoroethylene (PTFE).

In another embodiment, the present invention is a kit comprising a stent specially configured for placement at an anastomosis site in that the stent is curved along the longitudinal axis (endovascular implant), together with a sleeve comprising a biocompatible matrix material and a pharmaceutical agent, wherein the sleeve is applied to the external surface of the vessel or graft (perivascular implant), resulting in extravascular delivery of a pharmaceutical agent. The biocompatible matrix may be applied after the stent is deployed by a simple delivery device that permits folding of the limbs of the matrix to enable covering of the anastomosis. In another embodiment both the endovascular stent and the perivascular drug eluting biocompatible matrix material can be implanted during the time of surgery for creation of the anastomosis (e.g. AV graft, AV Fistula)

In another embodiment, the present invention is a kit comprising a stent specially configured for placement at an anastomosis site in that the stent is beveled, flared or trumpeted at the edge, together with a sleeve comprising a biocompatible matrix material and a pharmaceutical agent, wherein the sleeve is applied to the external surface of the vessel or graft, resulting in extravascular delivery of a pharmaceutical agent. The biocompatible matrix may be applied after the stent is deployed by a simple delivery device that permits folding of the limbs of the matrix to enable covering of the anastomosis. In another embodiment both the endovascular stent and the perivascular drug eluting biocompatible matrix material can be implanted during the time of surgery for creation of the anastomosis (e.g. AV graft, AV Fistula).

In another embodiment, the present invention is a kit comprising a stent specially configured for placement at an anastomosis site in that the stent is tapered together with a sleeve comprising a biocompatible matrix material and a pharmaceutical agent, wherein the sleeve is applied to the external surface of the vessel or graft, resulting in extravascular delivery of a pharmaceutical agent. The biocompatible matrix may be applied after the stent is deployed by a simple delivery device that permits folding of the limbs of the matrix to enable covering of the anastomosis. In another embodiment both the endovascular stent and the perivascular drug eluting biocompatible matrix material can be implanted during the time of surgery for creation of the anastomosis (e.g. AV graft, AV Fistula).

In another embodiment, the present invention is a kit comprising a stent specially configured for placement at an anastomosis site in that the stent is a covered stent (e.g. covered by PTFE) together with a sleeve comprising a biocompatible matrix material and a pharmaceutical agent, wherein the sleeve is applied to the external surface of the vessel or graft, resulting in extravascular delivery of a pharmaceutical agent. The biocompatible matrix may be applied after the stent is deployed by a simple delivery device that permits folding of the limbs of the matrix to enable covering of the anastomosis. In another embodiment both the endovascular stent and the perivascular drug eluting biocompatible matrix material can be implanted during the time of surgery for creation of the anastomosis (e.g. AV graft, AV Fistula).

In another embodiment, the present invention is a kit comprising a drug eluting balloon expandable stent and a self expanding nitinol stent specially configured for placement at an anastomosis site. The special features of the stent may include one or more of the following: curvature along the long axis of the stent, beveled, flared or trumpeted edge(s), tapered design, covering with a fabric (e.g. PTFE). Traditionally designed stents (e.g. balloon expandable stents such as stainless steel or cobalt chromium balloon expandable stents, self expanding stents such as nitinol self expanding stents, partially or completely biodegradable stents, stents that are partially or completely covered with a synthetic material such as PTFE or other biodegradable or non biodegradable polymers, or stents that are covered with a segment of biological tissue like a segment of vein, etc.) that do not have any of the features described above may also be included in the kit.

Methods for treating or preventing stenosis at an anastomosis site by applying the extravascular sleeve and the intravascular stent are also provided (FIGS. 12-15, 18 and 19). In one embodiment, the stent is inserted in its contracted state and manipulating a wire attached to the external surface of the stent pulls the exterior surface of the stent toward the interior wall of the vessel, resulting in expansion of the stent. In another embodiment, the stent is inserted in its contracted state and covered with a sheath, wherein retracting the sheath results in expansion of the stent. The system may be configured such that retraction of the sheath starts from the distal end (i.e. the distal end of the stent is deployed first), or, the system may be configured so that the retraction of the sheath begins from the proximal end (i.e. the proximal end of the stent is deployed first). (FIGS. 17A and 17B). In additional embodiments, the stent may be held in its compact, restrictive (non-expanded) state by other means (e.g. a wire wrapped around the stent, a membrane restricting expansion of the stent) prior to deployment. In one embodiment, the stent is a balloon-expandable stent. In another embodiment, the stent is self-expanding. In another embodiment, the stent delivery device permits the proximal end of the stent (closest to the operator's fingers) to be deployed first. Once the proximal end is released, it enables the operator to pull back and recognize that a few millimeters of the partially deployed stent are now on the arterial side of the anastomosis. At this point, the second mechanism of release allows the remaining portion of the stent to be released. In one iteration, the proximal end of the stent is released first, while in another iteration the distal end of the stent is released first.

The delivery system containing the stent may be introduced into the body percutaneously. The delivery system containing the stent may be introduced into the body during an open surgical procedure. The delivery system containing the stent may be introduced into the body using a robotic system The sleeve comprising a biocompatible matrix material and a pharmaceutical agent, may be implanted at the intended position during an open surgical procedure. The sleeve comprising a biocompatible matrix material and a pharmaceutical agent may also be implanted percutaneously. The sleeve comprising a biocompatible matrix material and a pharmaceutical agent may be implanted using a robotic system

BRIEF DESCRIPTION OF THE DRAWINGS

FIGS. 2A-2E illustrate how the stent design requirements (FIGS. 2A and 2B) are different for a right angled, non beveled anastomosis (FIG. 2C) and a beveled angled anastomosis (FIGS. 2D and 2E).

FIGS. 12A and 12B are 28 Day Angiograms from the two animals that received the endovascular self expanding nitinol stent 100 without the sirolimus eluting collagen matrix, which was placed at the anastomosis of the PTFE graft and the Vein. Narrowing within the stent is seen in both animals.

FIGS. 12C and 12D are 28 Day Angiograms are from the two animals that received the endovascular self expanding nitinol stent plus the Sirolimus eluting collagen matrix 200, which was placed at the anastomosis of the PTFE graft and the Vein.

In FIG. 13C, the Proximal Vein 115 is also visible. There is minimal narrowing of the stent.

FIG. 16A-16D shows the difference between a beveled stent edge and a traditional right angled stent edge and illustrates why the beveled edge provides optimal coverage of the anastomosis.

DETAILED DESCRIPTION

Figure 1C:
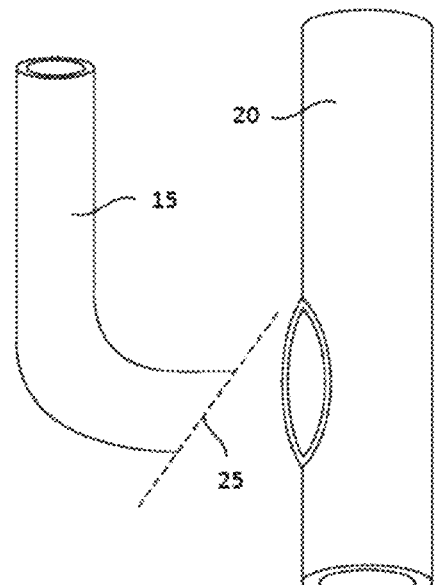
FIGS. 1A-1D illustrate the difference between a "non beveled" right angled anastomosis (FIGS. 1A and 1B) and a beveled, angled anastomosis (FIGS. 1C and 1D).

While the present invention is capable of being embodied in various forms, the description below of several embodiments is made with the understanding that the present disclosure is to be considered as an exemplification of the invention, and is not intended to limit the invention to the specific embodiments illustrated.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. As used herein, the terms "about" and "approximately" when referring to a numerical value shall have their plain and ordinary meanings to one skilled in the art of cardiology and pharmaceutical sciences or the art relevant to the range or element at issue. The amount of broadening from the strict numerical boundary depends upon several factors. For example, some of the factors to be considered may include the criticality of the element and/or the effect a given amount of variation will have on the performance of the claimed subject matter, as well as other considerations known to those of skill in the art. Thus, as a general matter, "about" or "approximately" broaden the numerical value, yet cannot be given a precise limit. For example, in some cases, "about" or "approximately" may mean±5%, or ±10%, or ±20%, or ±30% depending on the relevant technology. Also, the disclosure of ranges is intended as a continuous range including every value between the minimum and maximum values.

The medical devices of the present invention broadly comprise stents and sleeves used for treating stenosis at and around an anastomosis site. The present invention is unique in at least six respects: (1) the stent of the present invention is curved along its longitudinal axis ("candy cane shape") for special placement at a fistula or an anastomosis site, or to accommodate a vessel remote from the anastomosis site that has a curve (e.g. cephalic arch), (2) the stent of the present invention is beveled, flared or trumpeted for special placement and to facilitate alignment at a beveled anastomosis site, vessel origin (ostium) or vessel bifurcation wherein the side branch vessel originates at an angle other than a right angle from the parent vessel, (3) the stent of the present invention is tapered to facilitate placement wherein the diameter of the two structures are different, (4) the present invention includes a combination of drug-eluting balloon expandable or self-expanding stent and a plain, non-drug-eluting balloon expandable or self-expanding stent, (5) the stents of the present invention may be partially or completely covered with a fabric or polymer (e.g. PTFE), and (6) the methods and kits of the present invention combine the specially-configured stent with a sleeve that elutes a pharmaceutical agent directed to preventing stenosis. The drug-eluting sleeve may be used in combination with other self expanding and/or balloon expandable stents (i.e. it is not necessary to have a specifically configured stent to practice this invention).

Figure 1D:
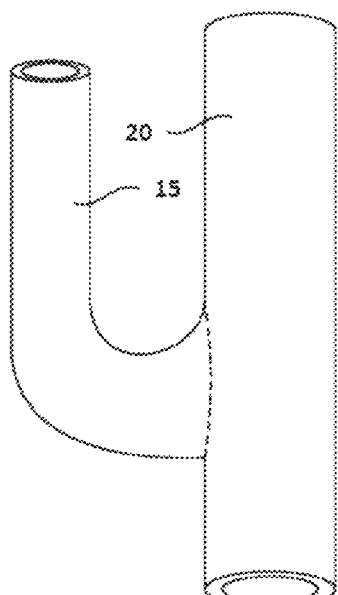
Figure 1A:
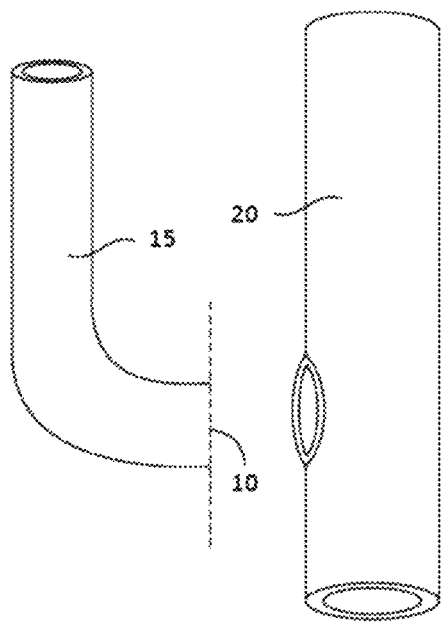
Figure 1B:
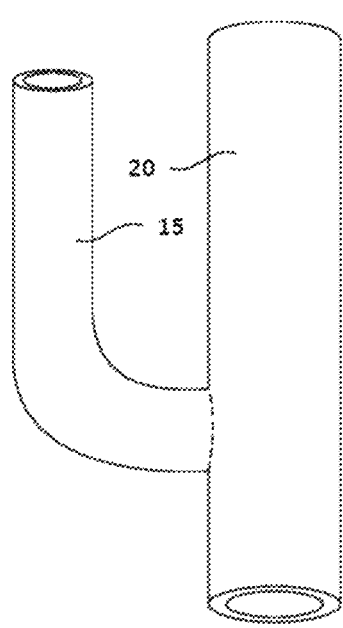
Figure 3:
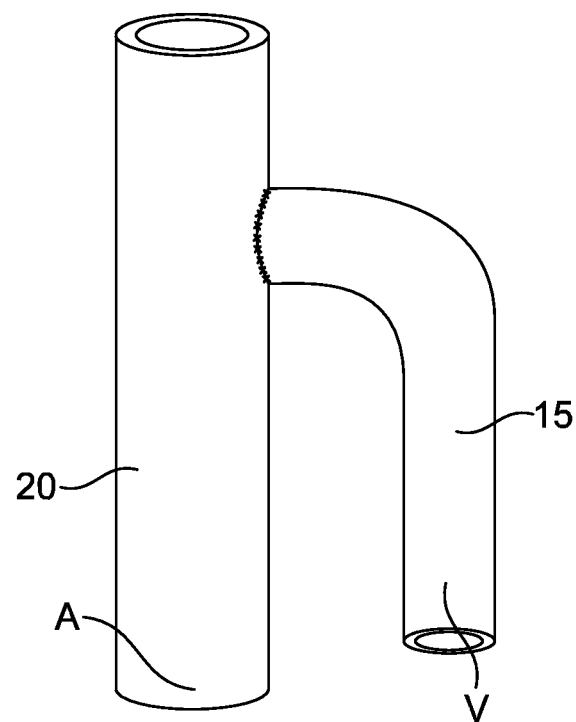
FIG. 3 is a side view of an arterio-venous fistula.

Referring to FIG. 1A, the edge 10 of the vessel or graft 15 may be cut (shown with the dashed lines) perpendicular to the longitudinal axis of the blood vessel or graft 10. In this instance, the anastomosis created by joining the two vessels, or a vessel and a graft, 15 and 20 (shown in FIG. 1B) will be at right angles. FIG. 1C shows that the edge 25 of the vessel or graft 15 may be also cut at an angle—this confers a beveled configuration to the end of the vessel 15. Notice that because of this bevel, the eventual size of the anastomosis (shown in FIG. 1D) is larger in terms of both length as well as the area of the anastomosis when compared to the right angled anastomosis shown in FIG. 1B. FIGS. 2A-2E illustrate some of the stent designs discussed in the present disclosure, that make the stent particularly suited for implant at and around the anastomosis. FIG. 2A shows a stent 30 that is essentially a tubular body with a longitudinal axis and a circular cross-section. The stent 30 has a degree of curvature along the longitudinal axis. The stent 30 has a first, proximal end 35 and a second, distal end 40, each of the ends 30, 35 having a different diameter 45, 50, conferring a tapered appearance to the stent 30. FIG. 2B shows the first end 35 of the stent 30 is flared or trumpeted. FIG. 2C illustrates how the stent 30 shown in FIG. 2A can be implanted in a right angled anastomosis. FIG. 2D illustrates that the stent 30 shown in FIG. 2A is not well suited for implantation around an anastomosis wherein the vein or graft 15 is beveled. FIG. 2E illustrates how a beveling, flaring, or trumpeting of the first end 35 of the stent 30 allows a more precise implantation at the anastomosis. FIG. 3 illustrates an anastomosis viewed from the side. The structure marked A represents an artery. The structure marked V represents a graft or vein. A and V can represent any hollow tube or conduit in the body undergoing an anastomosis.

Figure 4:
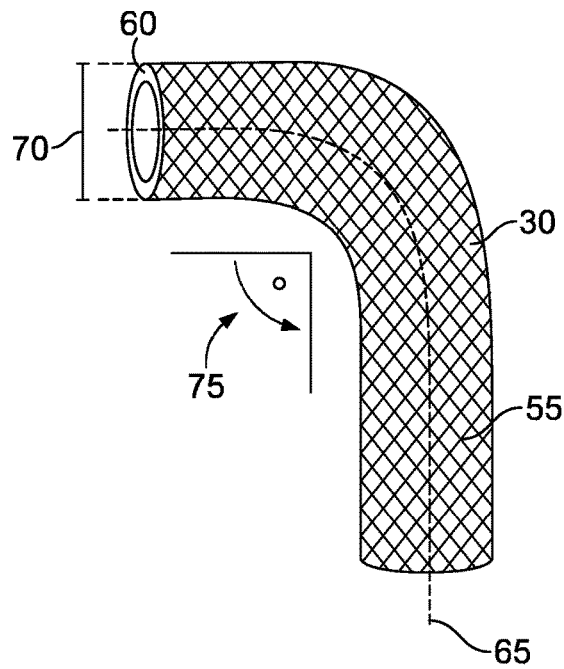
FIG. 4 is a side view of one embodiment of the stent of the present invention.
Figure 5:
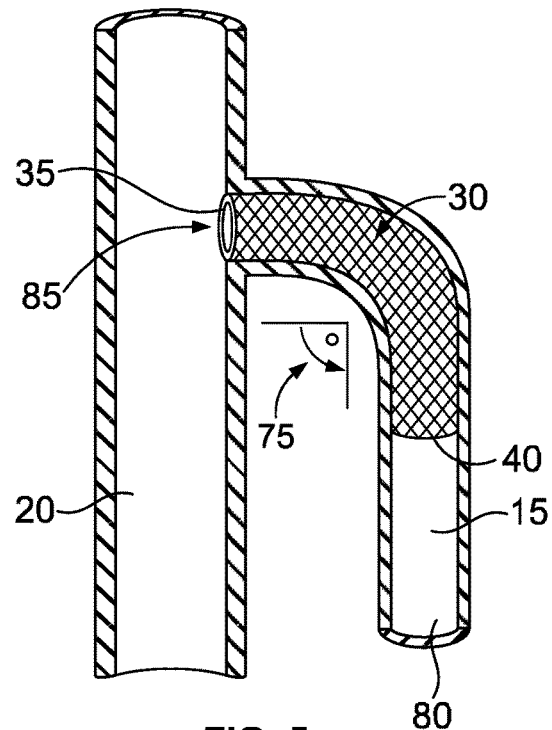
FIGS. 5-7 are side views of embodiments of the stent of the present invention in place at an arterio-venous fistula or across the anastomotic site of a graft, which has been transected along the longitudinal axis.

Referring to FIG. 4, in one embodiment, the stent 30 of the present invention has a web-like structure 55 defining an essentially tubular body having a tubular wall 60 with a longitudinal central axis 65 and a first end diameter 70, the web structure 55 being expandable from a contracted configuration to an expanded configuration, wherein the stent 30 is specially configured for placement at a fistula or an anastomosis site or a vessel with a curvature. The stent has a degree of curvature 75 along the longitudinal axis 65 between about 5 and 160 degrees. Referring to FIG. 5, the stent 30 is placed in the internal lumen 80 of the vein, graft or blood vessel 15 and the proximal end 35 of the stent 30 holds open the anastomosis orifice 85 at the junction of the vein, graft or blood vessel 15 and the artery, graft or blood vessel 20. The exact degree of curvature 75 of the stent 30 may be determined based upon the degree of curvature occurring in the vein 15. In cases other than fistula, reference numeral 15 can represent a graft or other blood vessel or conduit. The stent 30 is thus specially configured to maintain the structure of the anastomotic orifice 85 and the curvature of the vein or artery or other blood vessel 15 at a fistula or graft anastomosis site.

Figure 6:
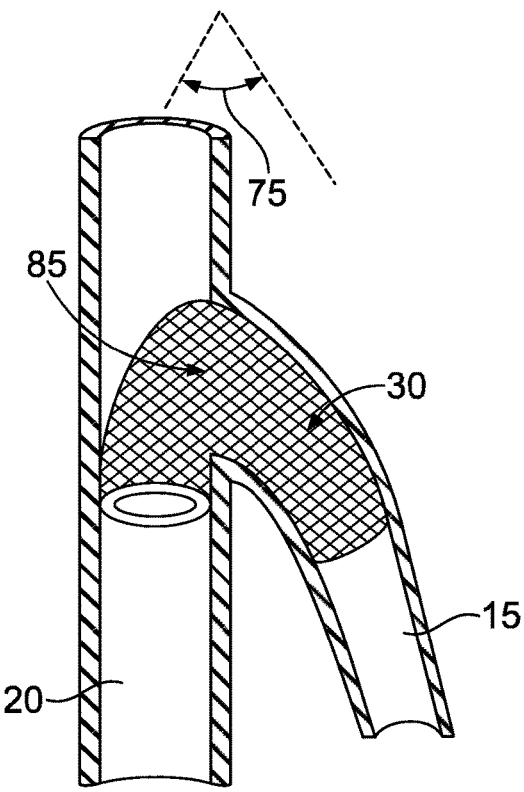

Referring to FIG. 6, the curved portion of the stent 30 may also be placed across the anastomosis or the graft orifice 85. In this placement, the stent 30 passes from the vein, graft or blood vessel 15, through the anastomosis orifice 85, and into the artery, graft or blood vessel 20. In the case of an AV graft, the structure labeled 20 will be a vein and the structure labeled 15 will be the prosthetic graft. In this instance (i.e. in the case of an AV graft), the stent 30 extends from the graft 15 across the anastomosis 85 and into the vein 20. In the case of an arterial bypass graft, the structure labeled 15 represents a prosthetic graft (e.g. PTFE), arterial conduit (e.g. the mammary artery) or a venous conduit (e.g. saphenous vein) and the structure marked 20 represents the recipient artery which may be a coronary artery or peripheral artery that is being bypassed. The degree of curvature 75 of the stent is between about 5 and 160 degrees and is selected based upon the degree of orientation between the vein, blood vessel or graft 15 and the artery, graft or other vascular structure 20. All embodiments described herein apply to either stent placement.

Figure 11:
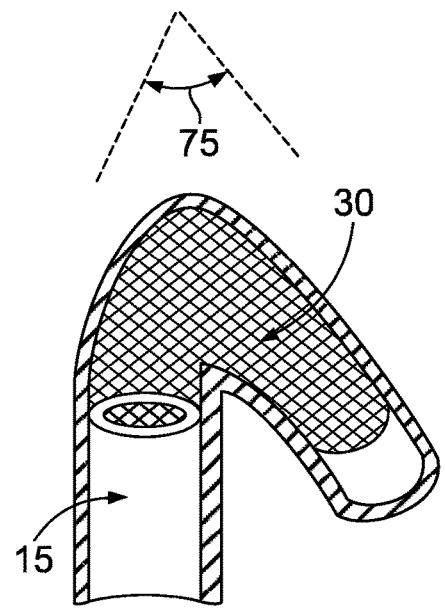
FIG. 11 is a side view of the embodiment of the stent of the present invention in place at a natural bend in a vessel, which has been transected along the longitudinal axis.

Referring to FIG. 11, the body of the stent 30 can also be placed at the natural bend of a blood vessel 15 at a location away from an anastomosis site. The degree of curvature 75 is between about 5 and 160 degrees and is selected based upon the degree of curvature in the vessel.

In a further embodiment of the present invention, the stent 30 is tapered so that the diameter decreases along the longitudinal axis 65 of the stent 30. Referring to FIG. 2A, the stent 30 is comprised of a first proximal end 35 and a second, distal end 40 opposite the proximal end 35. The diameter of the stent 30 at the proximal end 35 is greater than the diameter of the stent at the opposite, distal end 40. As is shown in FIG. 2C, this embodiment is particularly suited for placement in vessels where the diameter of the vessel changes from one segment to another.

In a further embodiment, the stent has a "beveled," "flared," or "trumpeted" edge 25. Referring to FIG. 2B, the stent 30 is comprised of a first proximal end 35 and a second, distal end 40 opposite the proximal end 35. At the proximal end 35 the web structure 55 expands outwardly, resulting in an increased diameter 45 at that end 35 of the stent 30, giving the proximal end 35 of the stent 30 a "beveled," "flared," or "trumpeted" appearance. As is seen in FIG. 2E, such an embodiment is particularly suited for placement at an anastamotic orifice 85. The beveled edge 25 allows the stent to abut the orifice 85 without protruding into the artery, vessel, or graft 20.

In a further embodiment, the stent elutes anti-vasculoproliferative drugs or agents such as rapamycin, paclitaxel, tacrolimus, everolimus, zotarolimus and other cell cycle inhibitor or similarly-functioning agents. This in combination with the special configuration of the stent 30, that allows accurate placement at the anastomosis (e.g. by beveling, flaring or trumpeting the edge) and close apposition to the inner surface of the curved blood vessel (by curving the stent along its longitudinal axis 65) allows for local delivery of antivasculoproliferative drugs directly to the immediate vicinity of the anastomosis orifice 85, preventing or suppressing or treating neointimal hyperplasia by delivery directly to the vascular structure an effective amount of an antiproliferative agent alone or in combination with adjuvants and other antiproliferative agents. Rapamycin (Sirolimus) is a preferred drug with antiproliferative properties for use with the present invention.

Figure 7:
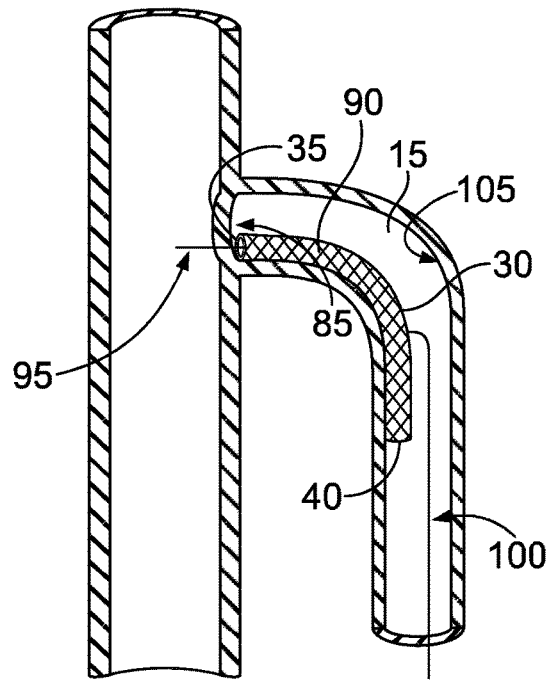

In one embodiment of the present invention, the stent 30 in its contracted state 90 is equipped with an external wire ("rip cord") to release and expand the stent. Referring to FIG. 7, the stent 30 in its contracted state is attached to a guidewire 95. A further wire 100 is attached to the external surface of the stent in its contracted state 90. Wire 100 may also be attached to the leading edge of the stent and not its surface. This wire 100 is configured so that, after the stent 30 is placed at the graft orifice or at the anastomosis site 85, manipulating the attached wire 100 pulls the external surface of the stent 30 toward the interior surface of the vessel or graft 15, causing the stent to expand and abut the interior surface 105 of the vessel or graft wall.

Figure 8:
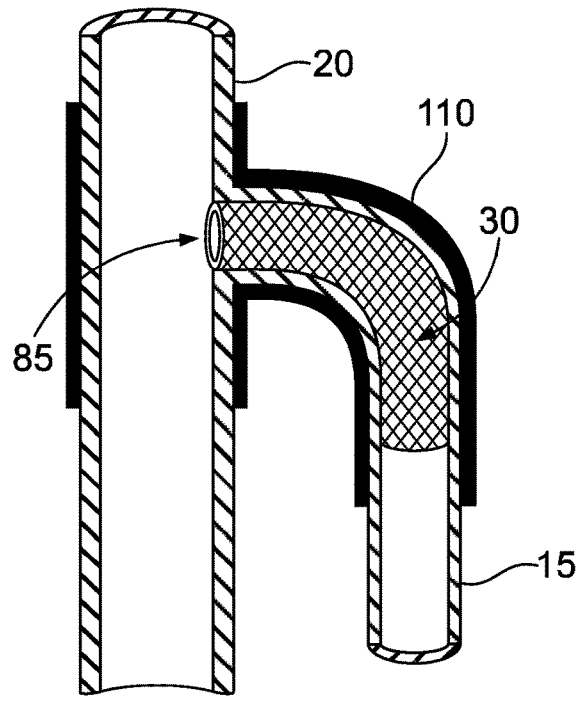
FIG. 8 is a side view of the kit of the present invention in use at an arterio-venous fistula, where the fistula and the wrap have been transected along the longitudinal axis to reveal placement of the stent.

Referring to FIG. 8, a further embodiment of the present invention is a kit for treating or preventing stenosis at an anastomosis site containing the previously described curved stent 30 specially configured for placement in an anastomosis site (bevel, flaring or trumpeting, tapering not shown in this figure) or any other type of balloon expandable or self-expanding stent, together with a wrap or sleeve 110, or an implantable prosthetic device for placement on the area surrounding the anastomotic orifice 85 and anastomosis site, on the outer surface of the vessel or graft 15 or 20, wherein the sleeve then elutes one or more antivasculoproliferative drugs or agents such as rapamycin (sirolimus), paclitaxel, tacrolimus, everolimus, zotarolimus and other cell cycle inhibitor or similarly-functioning agents. In addition to a biocompatible matrix material, e.g., protein, collagen, fibrin, chitosan, cellulose etc and an antiproliferative agent, this implantable device contains, optionally, agents that inhibit collagen accumulation in the tunica media and adventitia of the vascular wall and pharmaceuticals that help reduce calcification of the vascular wall. Rapamycin is a preferred drug with antiproliferative properties for use with the present invention. The rapamycin diffuses from the outside and through the vessel and/or graft wall to the interior of the vein and/or artery and/or graft. Elution of rapamycin (and other drugs with antiproliferative effect) into and through the vascular wall from the outside starts soon after the device is implanted and the drug will inhibit smooth muscle cell proliferation at the anastomosis site.

The kit of the present invention thus improves the treatment and/or prevention of stenosis by providing a novel treatment originating from within the vascular or graft lumen in combination with an extravascular pharmaceutical application. This combination can prevent stenosis of the vein, graft, artery and anastomotic orifice as well as treat the restenosis that commonly follows stent implantation. In another embodiment of the invention, the specially configured stent is drug eluting, resulting in intravascular delivery of pharmaceutical agents directly to the vicinity of the graft orifice in addition to the extravascular pharmaceutical treatment provided by the sleeve.

The entire contents of U.S. Pat. No. 6,726,933, entitled "Apparatus and Methods for Preventing or Treating Failure of Hemodialysis Vascular Access and Other Vascular Grafts," and U.S. Patent Application Publication No. 2005/0004158, entitled "Medical Implants and Methods For Regulating the Tissue Response to Vascular Closure Devices" are hereby incorporated by this reference.

The method of the present invention discloses providing a stent 30 that is specially configured for placement at an anastomosis site as described above, providing a sleeve 110 comprising a biological matrix imbibed with a pharmaceutical agent, applying the sleeve to the extravascular surface of an anastomosis site, and inserting the stent 30 to the vein, vessel and graft 15 and orifice 85 of an anastomosis site. In one embodiment, the stent 30 is configured with an external wire 100 affixed to the outer surface of the stent 30. As to FIG. 7, the stent 30 in its contracted state 90, is then inserted into the vein, graft or blood vessel 15 through the use of a guide wire 95. After the proximal end 35 of the stent is in place at the anastomotic orifice 85 or at the anastomosis site, the wire 100 affixed to the external surface of the stent is manipulated, pulling the external surface of the stent toward the interior surface 105 of the vessel, causing the stent 30 to expand and abut the interior surface 105 of the wall of the vessel or graft 15.

Figure 9:
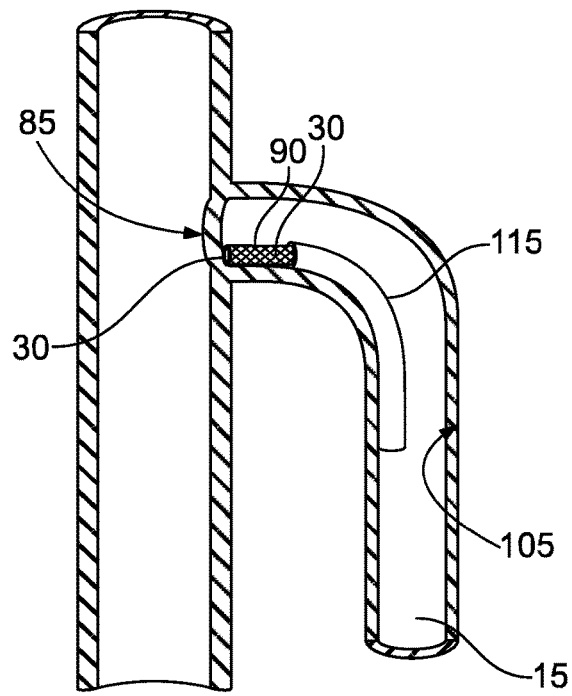
FIG. 9 is a side view of one embodiment of the method of the present invention, where the arterio-venous fistula has been transected to reveal placement of the stent delivery system.

As to FIG. 9, in another embodiment, the stent 30 is inserted its contracted state 90, and is held in its contracted state by a sheath 115 surrounding the contracted stent 90. After the proximal end 35 of the stent 30 is placed at the anastomotic orifice 85 or anastomosis site, the sheath 115 is retracted. Retraction of the sheath 115 causes the stent 30 to expand and abut the interior surface 105 of the wall of the vessel or graft 15. Finally, the sheath 115 is removed, leaving the expanded stent 30 in place at the anastomosis site.

In one embodiment, the stent is a balloon-expandable stent. In anther embodiment, the stent is a self-expanding stent.

Figure 10:
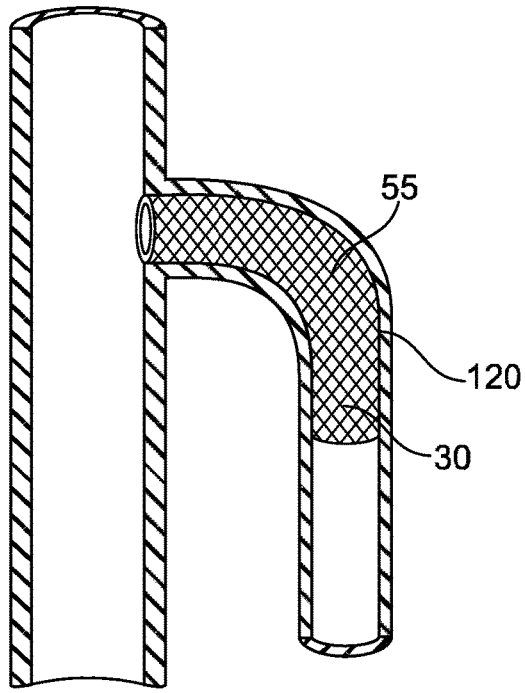
FIG. 10 is a side view of a covered stent, which has been transected along the longitudinal axis.

As to FIG. 10, in another embodiment, the external surface of the web structure 55 of the balloon expandable or self expandable stent 30 may be partially or completely covered by a polymer, fabric or biological coating 120. An example of such a covering that may be used for the stent is polytetrafluoroethylene (PTFE).

In another embodiment, the invention relates to the use of a plain stent (i.e., non-drug coated self-expanding or balloon expanding stent) at and around the anastomotic site of an AV fistula as a stand-alone treatment for fistula outflow stenosis. Such method may be used to treat outflow stenosis prophylactically shortly after the surgery with a plain stent without the perivascular application of a drug-eluting sleeve. In other words, the use of the sleeve is optional. Such plain stent can be an existing stent design or any of the novel stent designs described elsewhere herein.

Additionally, the order of the steps of the methods is not critical to the novelty thereof.

FIGS. 16A-16D show the difference between a beveled stent edge and a traditional right angled, square-cut stent edge and illustrates why the beveled edge provides optimal coverage of the anastomosis when the vessels of the anastomosis are not joined perpendicular to each other. Since neither of the situations in FIG. 16A (i.e. the square ended stent is placed at a location such that it is too short to completely contact the full circumference of the anastomosis orifice and does not extend all the way down to the site of the anastomosis) or FIG. 16 B (i.e. in order to reach the full circumference of the anastomosis orifice, the stent must protrude into the vessel past the anastomosis) is desirable, a stent with a "beveled," "flared" or "trumpeted" edge can overcome this problem. The "bevel" helps in providing optimal coverage of the anastomosis and will facilitate stent deployment such that the anastomosis is completely covered without protrusion into the adjacent vessel (see FIG. 16C).

Figure 17A:
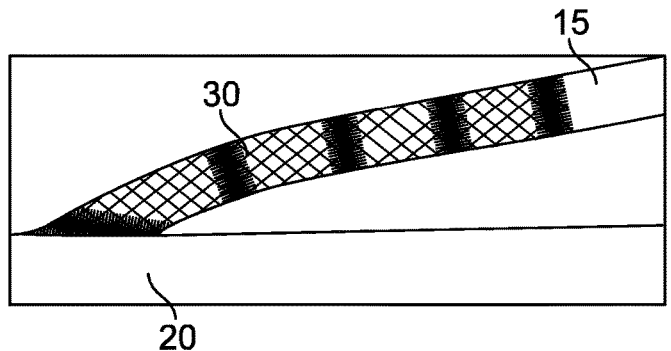
FIGS. 17A-17F illustrates the difference between the traditional, conventional deployment system for a self expanding stent (distal end deployed first, proximal end deployed last) and the proposed deployment system, which allows "proximal end first distal end last" deployment of the stent.
Figure 17A:
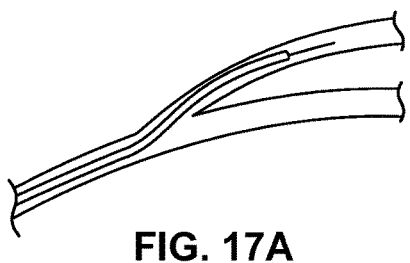
Figure 17B:
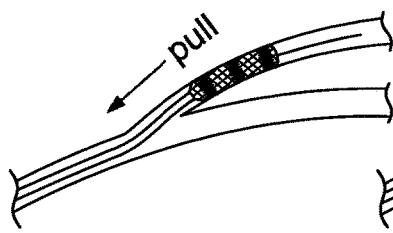
Figure 17C:
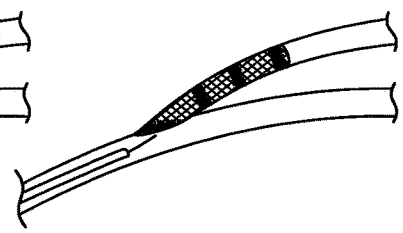
Figure 17D:
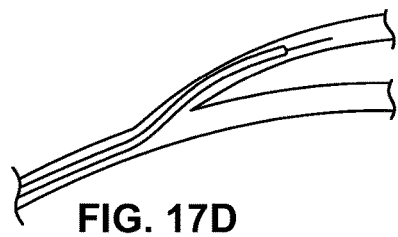
Figure 17E:
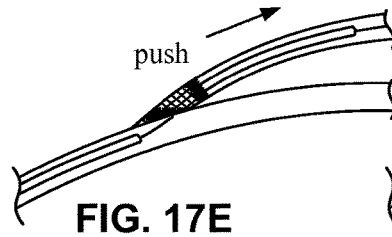
Figure 17F:
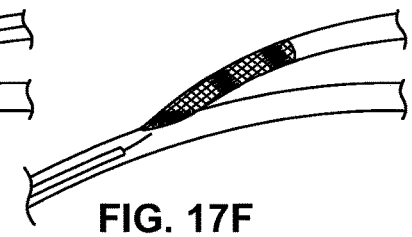

FIGS. 17A-17E illustrate the difference between the traditional, conventional deployment system for a self expanding stent (see FIGS. 17A-17C, depicting conventional delivery method in which the distal end of the stent is deployed first and the proximal end is deployed last) and the proposed delivery system (see FIGS. 17D-17F, depicting proposed delivery method in which the proximal end of the stent is deployed first and the distal end is deployed last).

Figure 18A:
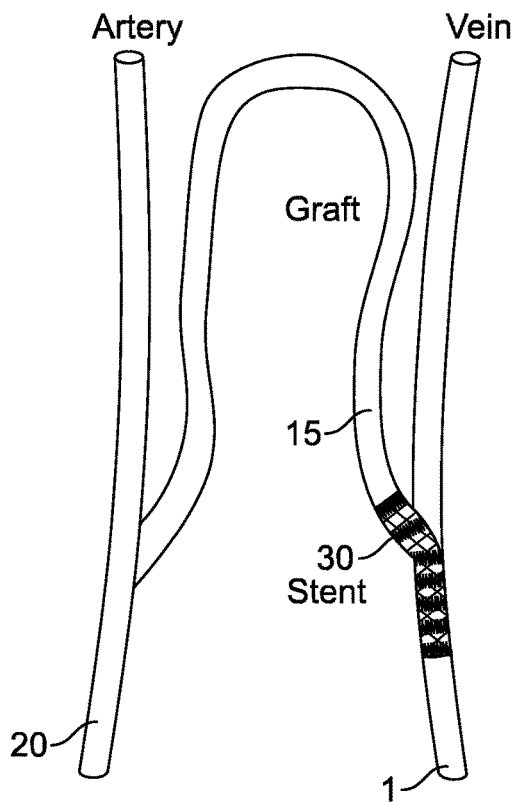
FIGS. 18A-18B and 19A-19B illustrate the concept of combining an endovascular stent together with a perivascular drug eluting matrix, both implants placed at and around the anastomosis.
Figure 18B:
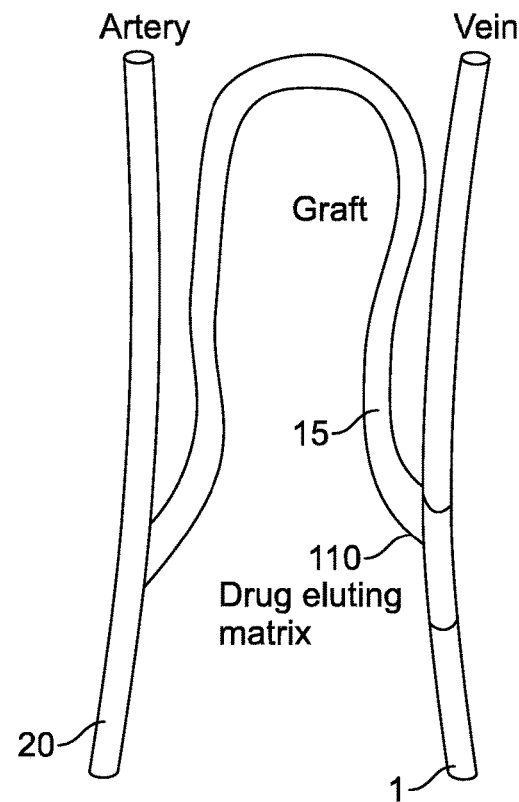

FIG. 18 illustrates how an endovascular stent 30 will be used with a perivascular drug eluting matrix 110 with an AV Graft. The AV graft is constructed by anastomosing a piece of PTFE graft 15 between an artery 20 and a vein 20. The stent 30 is placed internally at and around the site of anastomosis (see FIG. 18A). The drug eluting matrix 110 is placed on the external aspect of the blood vessel 20 and graft 15 (see FIG. 18B). FIG. 18 illustrates this use at the graft venous anastomosis. The implants can also be done at the graft arterial anastomosis or elsewhere in the AV graft system. This stent 30 and dug eluting matrix 110 configuration was used in the therapeutic example discussed in Sections 64-73 under Therapeutic Example (AV Graft)

Figure 19A:
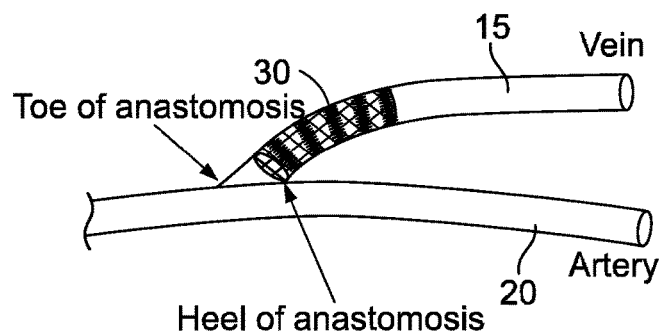
Figure 19B:
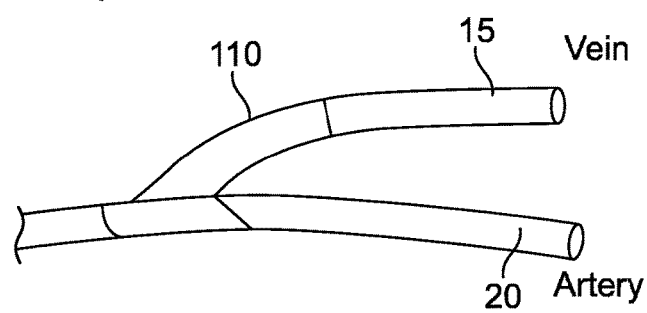

FIG. 19 illustrates how an endovascular stent will be used with a perivascular drug eluting matrix for an AV Fistula. The AV fistula is constructed by anastomosing the end of a segment of vein 15 to the side of an artery 20. The stent 30 shown in this illustration is a traditional non beveled stent, placed internally at and around the site of anastomosis and extending into the outflow vein 15 (see FIG. 19A). The drug eluting matrix 110 is placed on the external aspect of the blood vessel (see FIG. 19B). These same concepts can be practiced with the specially designed stents disclosed in this invention. This stent 30 and dug eluting matrix 30 configuration was used in the therapeutic example discussed in Sections 74-82 under Therapeutic Example (AV Fistula)

Therapeutic Example (AV Graft)

Methods: A proof of principle study was performed using an ovine model. A 6 mm PTFE vascular graft was anastomosed between the carotid artery on one side and the contralateral jugular vein, creating an arterio venous (AV) loop graft that is similar in construction to the human hemodialysis access loop. A total of four animals were studied, two animals (two AV grafts) received an endovascular self expanding nitinol stent at the PTFE graft-venous anastomosis, the other two animals (two AV grafts) received an endovascular self expanding nitinol stent at the PTFE-venous graft anastomosis plus a perivascular sirolimus (rapamycin) eluting collagen matrix. The sirolimus eluting collagen matrix was implanted on the external surface of the PTFE graft venous anastomosis location, such that the matrix on the external aspect roughly corresponded to the location of the endovascular nitinol endovascular stent. The stent used was a self expanding nitinol stent, 30 mm in length and fully expanded had a diameter of 8.0 mm. The collagen matrix was combined with a known dose of sirolimus (approximately 75 microgram/cm$^2$).

Results: Contrast Angiography was performed to assess status of the graft, stent and the vessel at 28 and 56±1 day after initial surgery.

A. Results of Angiography after 28 Days are Shown in FIG. 12.

FIGS. 12A, 12B: These figures are 28 Day Angiograms from the two animals that received the endovascular self expanding nitinol stent 100 without the sirolimus eluting collagen matrix, which was placed at the anastomosis of the PTFE graft and the Vein. Narrowing within the stent is seen in both animals.

FIGS. 12C, 12D: These figures are 28 Day Angiograms are from the two animals that received the endovascular self expanding nitinol stent plus the Sirolimus eluting collagen matrix 200, which was placed at the anastomosis of the PTFE graft and the Vein. There is no angiographically obvious narrowing in FIG. 1C and minimal narrowing of the stent lumen in FIG. 1D.

B. Results of Angiography after 56 Days are Shown in FIG. 13.

Figure 13A:
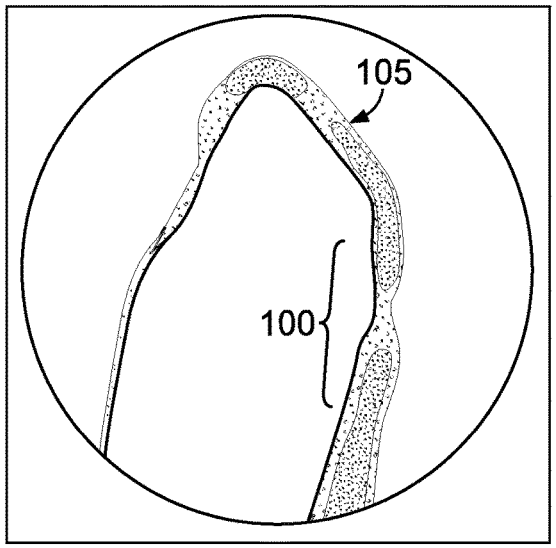
FIGS. 13A and 13B are 56 Day Angiograms from the two animals that received the endovascular self expanding nitinol stent 100 without the Sirolimus eluting collagen matrix, which was placed at the anastomosis of PTFE graft 105 and the Vein 110. Narrowing of the stent is seen and is more pronounced compared to the appearance at 28 days.
Figure 13B:
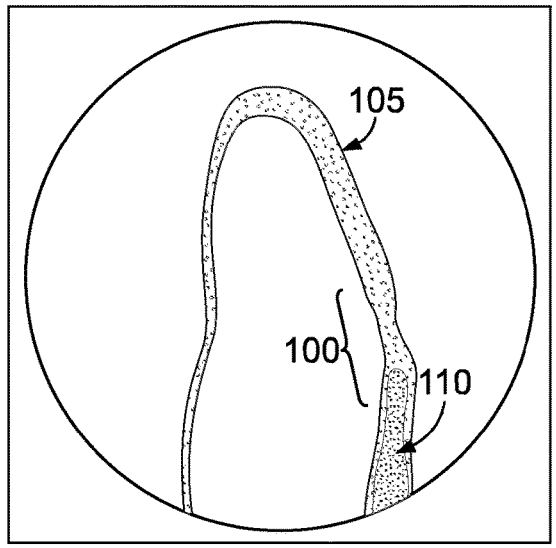

FIGS. 13A, 13B: These figures are 56 Day Angiograms from the two animals that received the endovascular self expanding nitinol stent 100 without the Sirolimus eluting collagen matrix, which was placed at the anastomosis of PTFE graft 105 and the Vein 110. Narrowing of the stent is seen and is more pronounced compared to the appearance at 28 days.

Figure 13C:
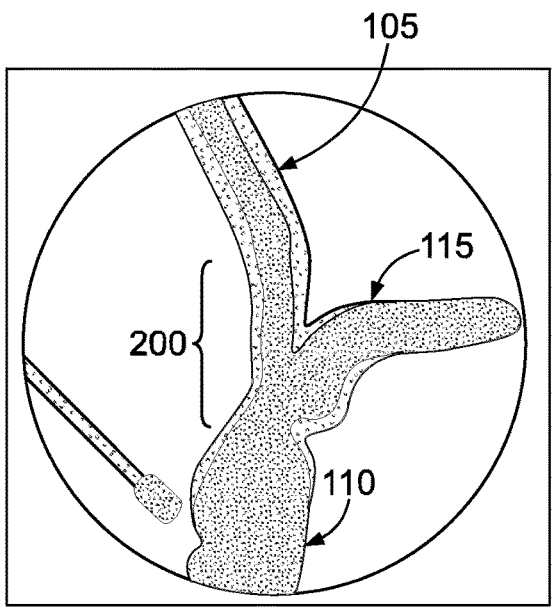
FIGS. 13C and 13D are 56 Day Angiograms from the two animals that received the endovascular self expanding nitinol stent plus the Sirolimus eluting collagen matrix 200, which was placed at the anastomosis of the PTFE graft 105 and the Vein 110.
Figure 13D:
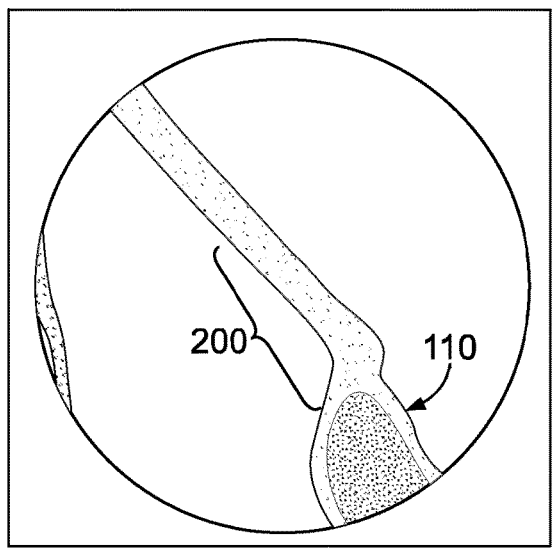

FIGS. 13C, 13D: These figures are 56 Day Angiograms from the two animals that received the endovascular self expanding nitinol stent plus the Sirolimus eluting collagen matrix 200, which was placed at the anastomosis of the PTFE graft 105 and the Vein 110. In FIG. 13C, the Proximal Vein 115 is also visible. There is minimal narrowing of the stent.

Approximate measurements based on offline measurements are shown in the Table below. All stent dimensions were normalized to the known graft dimension of 6.0 mm.

| Animal ID | 28 Days | Assigned Treatment | Nominal Graft Diameter (mm) | Minimal Stent Lumen Dimension (MLD mm) | Stent % Diameter stenosis |
|---|---|---|---|---|---|
| 9S003 | FIG. 12A | AV Graft + Stent | 6.0 | 3.0 | 50% |
| 9S004 | FIG. 12B | AV Graft + Stent | 6.0 | 2.4 | 60% |
| 9S014 | FIG. 12C | AV Graft + Stent + (Collagen matrix + Sirolimus) | 6.0 | 6.0 | 0 |
| 9S015 | FIG. 12D | AV Graft + Stent + (Collagen matrix + Sirolimus) | 6.0 | 5.0 | 17% |

| Animal ID | 56 ± 1 Days | Assigned Treatment | Nominal Graft Diameter (mm) | Minimal Stent Lumen Dimension (MLD; mm) | Stent % Diameter stenosis |
|---|---|---|---|---|---|
| 9S003 | FIG. 13A | AV Graft + Stent | 6.0 | 1.5 | 75% |
| 9S004 | FIG. 13B | AV Graft + Stent | 6.0 | 2.1 | 65% |
| 9S014 | FIG. 13C | AV Graft + Stent + (Collagen matrix + Sirolimus) | 6.0 | 5.4 | 10% |
| 9S015 | FIG. 13D | AV Graft + Stent + (Collagen matrix + Sirolimus) | 6.0 | 4.5 | 25% |

Conclusions

1. The degree of narrowing (% stent diameter stenosis) is more in the animals that received the stent without the drug eluting collagen matrix in comparison to the animals that received both the stent as well as the drug eluting stent matrix.
2. The residual minimal stent lumen dimension (MLD) is greater in the animals that received the stent with the drug eluting collagen matrix in comparison to the animals that received the stent without the drug eluting stent matrix.
3. These differences in stent % diameter stenosis as well as the minimal stent lumen dimensions (MLD) are seen at both 28 days as well as at 56±1 days after the index surgery.

Therapeutic Example (AV Fistula)

Methods: A proof of principle study was performed using an ovine arterio-venous fistula model. Bilateral arterio venous fistula were created by anastomosing the femoral vein to the femoral artery in an end (of vein) to side (of artery) fashion. The method of anastomosis (end to side) mimics the configuration of the AV fistulae created for providing dialysis access in humans (e.g. radio-cephalic, brachio-cephalic). The concept of using the endovascular stent plus the perivascular drug eluting (e.g. sirolimus) can be applied to other anastomotic configurations as well (e.g. end to end, side to side etc) as well as other surgeries were a vein and an artery are anastomosed (e.g. Coronary artery bypass graft surgery, peripheral vascular bypass surgery) or other surgeries where two conduits are anastomosed (e.g. fallopian tubes, ureter, biliary duct, bronchial airways, intestinal loops etc) Control fistulae received neither the endovascular self-expanding nitinol stent nor the perivascular sirolimus (rapamycin) eluting collagen matrix. Treated fistulae received an endovascular self expanding nitinol stent starting from the anastomosis and extending out to the outflow vein (in this instance covering the juxta-anastomotic segment) plus a perivascular sirolimus (rapamycin) eluting collagen matrix. The sirolimus eluting collagen matrix was implanted on the external surface of the fisulae, such that the matrix on the external aspect roughly corresponded to the anastomotic location of the endovascular nitinol endovascular stent. A sirolimus eluting matrix was also implanted at the anastomosis such that the matrix wrapped both the artery as well as the vein at that location. The illustrative example discussed below shows the use of a self-expanding stent 30 mm or 40 mm in length and a fully expanded diameter of 6 mm. The collagen matrix was combined with a known dose of sirolimus (approximately 75 microgram/cm$^2$).

Results: Contrast Angiography was performed to assess status of the fistulae, anastomosis, stent and the vessel (controls and treated) on day 0 (day of surgery) and 28 days after surgery. An angiogram was also performed 62 day after surgery in the treated animal example discussed below.

A. Results of Angiography on Day 0 (Day of Surgery) are Shown in FIG. 14.

Figure 14A:
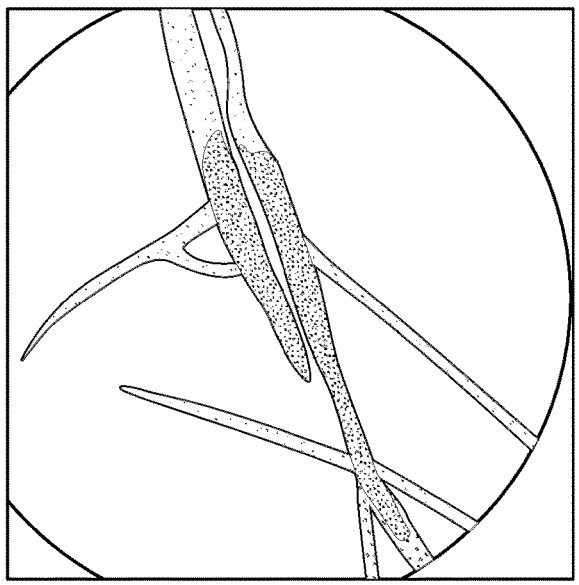
FIGS. 14A and 14B are Angiograms of control AV fistulae (the left and right AV fistula, respectively) in Animal ID No. 9S005, which do not include a stent or siroliums eluting matrix, from the day of surgery (Day 0).
Figure 14B:
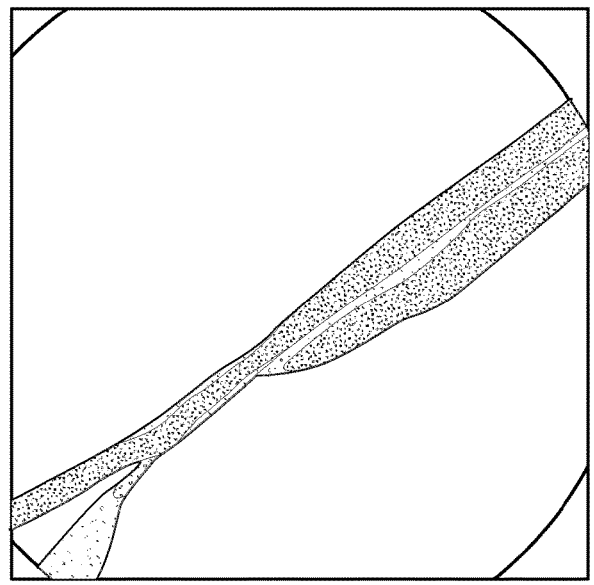

FIGS. 14A, 14B: These figures are Angiograms of control AV fistulae (the left and right AV fistula, respectively) in Animal ID No. 9S005, which do not include a stent or siroliums eluting matrix, from the day of surgery (Day 0).

Figure 14C:
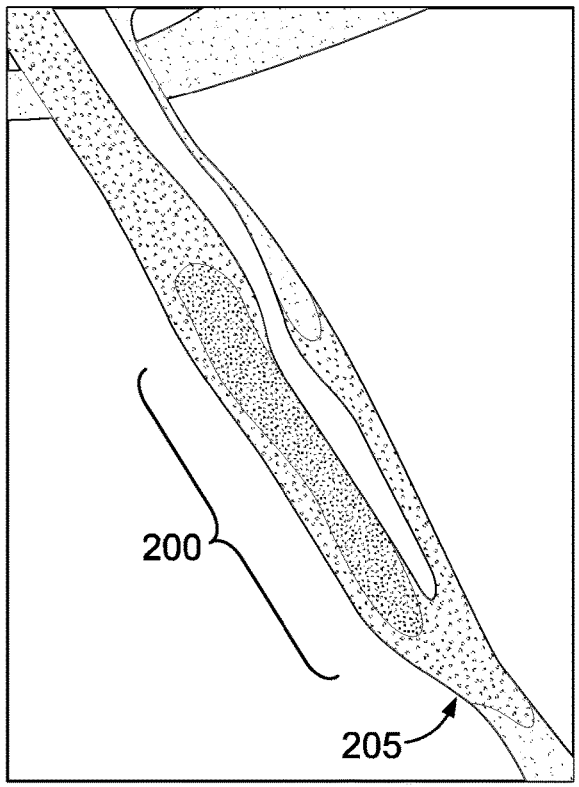
FIGS. 14C and 14D are Angiograms from the day of surgery (Day 0) for Animal ID No. 9S019, which was treated with an endovascular self-expanding stent (6 mm×30 mm for the left AV fistula, and 6 mm×40 mm for the right AV fistula) and Perivascular Sirolimus Eluting Matrix 200. The anastomosis 205 is also visible in each Angiogram.
Figure 14D:
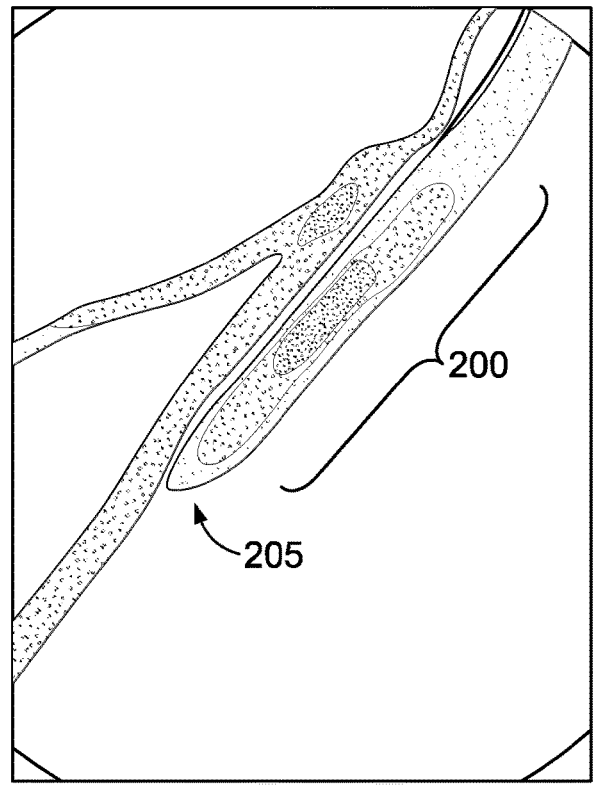

FIGS. 14C, 14D: These figures are Angiograms from the day of surgery (Day 0) for Animal ID No. 9S019, which was treated with an endovascular self-expanding stent (6 mm×30 mm for the left AV fistula, and 6 mm×40 mm for the right AV fistula) and Perivascular Sirolimus Eluting Matrix 200. The anastomosis 205 is also visible in each Angiogram.

B. Results of Follow Up Angiography are Shown in FIG. 15.

Figure 15A:
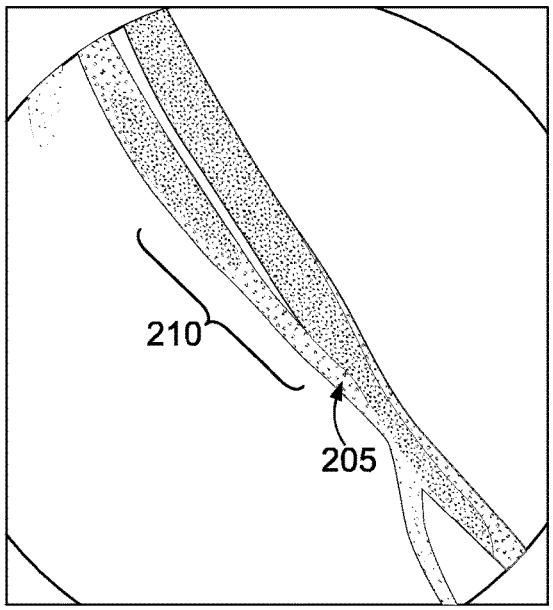
FIGS. 15A and 15B are Angiograms of control AV fistulae (the left and right AV fistula, respectively) in Animal ID No. 9S005, which do not include a stent or sirolimus eluting matrix, taken 28 days following surgery that show severe stenosis of the outflow vein 210 (juxta anastomotic segment) as well as the anastomosis 205.
Figure 15B:
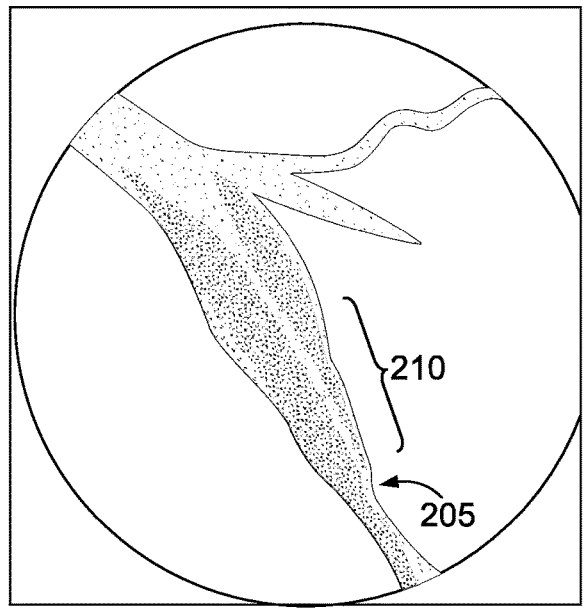

FIGS. 15A, 15B: These figures are Angiograms of control AV fistulae (the left and right AV fistula, respectively) in Animal ID No. 9S005, which do not include a stent or sirolimus eluting matrix, taken 28 days following surgery that show severe stenosis of the outflow vein 210 (juxta anastomotic segment) as well as the anastomosis 205.

Figure 15C:
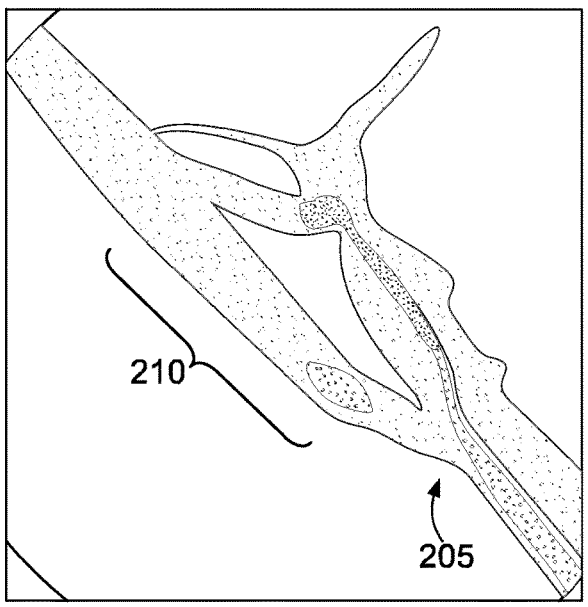
FIGS. 15C and 15D are Angiograms of the left AV fistula performed on day 28 (FIG. 15C) and day 62 (FIG. 15D) in Animal ID No. 9S019 that was treated with endovascular self-expanding stent (6 mm×30 mm and Perivascular Sirolimus Eluting Matrix 200. On day 28, significant improvement in lumen dimensions of the anastomosis 205 as well as the outflow vein (improved patency) is seen in comparison to controls. The improvement is maintained on the angiogram performed on day 62.
Figure 15D:
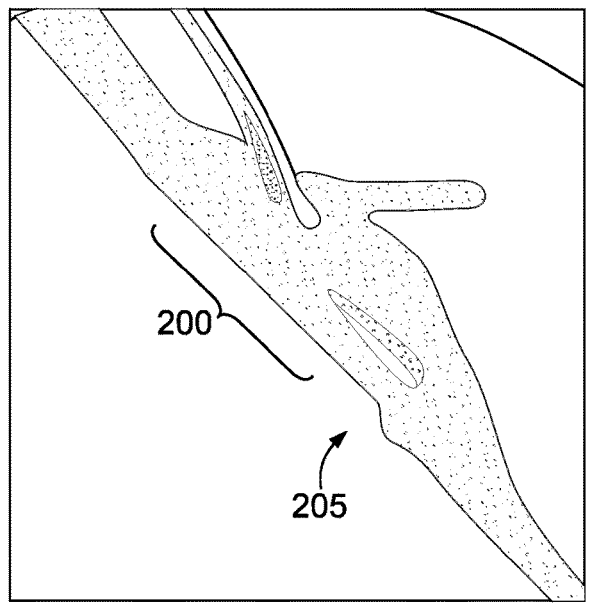
Figure 16A:
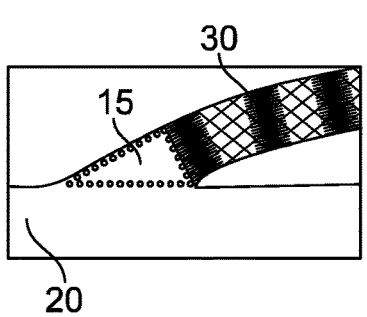
Figure 16B:
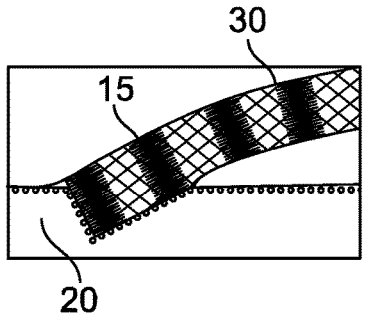
Figure 16C:
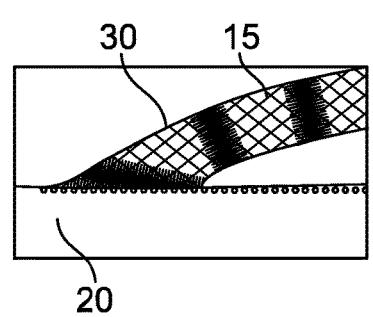

FIGS. 15C, 15D: These figures are Angiograms of the left AV fistula performed on day 28 (FIG. 15C) and day 62 (FIG.

15D) in Animal ID No. 9S019 that was treated with endovascular self-expanding stent (6 mm×30 mm and Perivascular Sirolimus Eluting Matrix 200. On day 28, significant improvement in lumen dimensions of the anastomosis 205 as well as the outflow vein (improved patency) is seen in comparison to controls. The improvement is maintained on the angiogram performed on day 62.

Conclusions 1. 28-day angiograms of the Arterio-venous fistulae in the control animal (no endovascular stent or perivascular sirolimus eluting collagen matrix) show severe stenosis at the anastomosis as well as the juxta anastomotic segment of the outflow vein. This pattern of stenosis mimics the situation in humans (e.g. stenosis in radiocephalic fistulae created for supporting dialysis, anastomotic stenosis of vein grafts in coronary artery and peripheral artery bypass graft surgery)
2. Treated animal (endovascular stent plus perivascular sirolimus eluting collagen matrix) shows significant improvement in lumen dimensions (improved lumen patency) at the anastomosis as well as the outflow vein.
3. This benefit is seen in both the 28 day as well as the 62 day angiograms.

All documents cited herein, including the foregoing, are incorporated herein by reference in their entireties for all purposes.

The invention claimed is:

1. A method for preventing stenosis in a vascular structure having an anastomosis wherein the vascular structure is an artery, a vein or a graft, the method comprising the steps of:
 a. forming an anastomosis;
 b. deploying a drug-free stent within the lumen of the vascular structure at or in the vicinity of the anastomosis; and
 c. applying locally and externally to the vascular structure containing the stent an effective amount of rapamycin or an analogue of rapamycin via a biocompatible matrix material that carries the rapamycin or analogue of rapamycin;
 wherein the steps of the method are performed in a single surgical procedure.

2. The method of claim 1 wherein the anastomosis results from the formation of an arterio-venous fistula, or an arterio-venous graft or an arterial-arterial graft.

3. The method of claim 1 wherein the matrix material carries about 75 micrograms per cm² of the rapamycin or analogue of rapamycin.

4. The method of claim 1 wherein the analogue of rapamycin is everolimus or zotarolimus.

5. The method of claim 1 wherein the matrix material is selected from the group consisting of collagen, fibrin, polysaccharide and mixtures thereof.

6. The method of claim 5 wherein the matrix material comprises collagen.

7. The method of claim 6 wherein the collagen is selected from the group consisting of Type I, Type II, Type III, Type IV, Type XI and mixtures thereof.

8. The method of claim 7 wherein the collagen is Type I Bovine collagen.

9. The method of claim 5 wherein the polysaccharide is chitosan.

10. The method of claim 1 wherein the stent is curved along the longitudinal axis.

11. The method of claim 1 wherein the stent is partially or completely covered by a polymer or fabric.

12. The method of claim 11 wherein the cover is PTFE.

13. The method of claim 1 wherein the stent is a self-expanding or a balloon expanding stent.

14. The method of claim 1 wherein the stent is beveled, flared or trumpeted.

15. The method of claim 14 wherein the stent is beveled.

16. A method for preventing stenosis in a vascular structure having an anastomosis wherein the vascular structure is an artery, a vein or a graft, comprising the steps of:
 a. forming an anastomosis;
 b. deploying a drug-free stent within the lumen of a vascular structure at or in the vicinity of the anastomosis; and
 c. applying a sleeve locally and externally to the vascular structure containing the stent, the sleeve consisting essentially of a biocompatible matrix material and an anti-vasculoproliferative drug;
 wherein the steps of the method are performed in a single surgical procedure.

17. The method of claim 16 wherein the anastomosis results from the formation of an arterio-venous fistula, or an arterio-venous graft or an arterial-arterial graft.

18. The method of claim 16 wherein the matrix material carries about 75 micrograms per cm² of the anti-vasculoproliferative drug.

19. The method of claim 16 wherein the anti-vasculoproliferative drug is rapamycin or an analogue of rapamycin.

20. A method for preventing stenosis in a vascular structure having an anastomosis wherein the vascular structure has an external surface, comprising the steps of:
 a. Forming an anastomosis;
 b. Inserting a drug-free stent into the vascular structure at or in the vicinity of the anastomosis wherein the stent comprises a structure defining an essentially tubular body with a longitudinal axis and a circumferential diameter, the structure being expandable from a contracted configuration to an expanded configuration, wherein the stent is beveled at an edge and/or curved along the longitudinal axis for placement at or in the vicinity of the anastomosis; and
 c. Applying a sleeve to the external surface of the vascular structure containing the stent, wherein the sleeve comprises a biocompatible matrix material imbibed with an anti-proliferative agent;
 wherein the steps of the method are performed in a single surgical procedure.

21. The method of claim 20, wherein the vascular structure is a vein, an artery or a graft.

22. The method of claim 20, wherein the anti-proliferative agent is selected from the group consisting of rapamycin, everolimus, zotarolimus or other analogue of rapamycin.

23. The method of claim 20, wherein the matrix material is selected from the group consisting of collagen, fibrin, polysaccharide and mixtures thereof.

24. The method of claim 23, wherein the matrix material comprises collagen.

25. The method of claim 24, wherein the collagen is selected from the group consisting of Type I, Type II, Type III, Type IV, Type XI and mixtures thereof.

26. The method of claim 25, wherein the collagen is Type I Bovine collagen.

27. The method of claim 20, wherein the stent is partially or completely covered by a polymer or fabric.

28. The method of claim 27, wherein the covering is PTFE.

29. The method of claim 20, wherein the stent further comprises an external wire affixed to the stent in its compressed state, and wherein inserting the stent further comprises the steps of:
   a. Inserting the stent in its contracted state into the vascular structure; and
   b. Manipulating the external wire to allow the stent to expand and to allow the external surface of the stent to come in contact with the internal surface of the vascular structure.

30. The method of claim 22, wherein the rapamycin or an analogue of rapamycin is present in an amount of about 75 micrograms per $cm^2$.

31. A method for preventing stenosis in a vascular structure having an anastomosis wherein the vascular structure is an artery, a vein or a graft, the method comprising the steps of:
   a. Forming an anastomosis;
   b. Deploying a self-expanding stent within the vascular structure at or in the vicinity of the anastomosis, wherein the stent has a longitudinal axis and a circumferential diameter, the stent being expandable from a contracted configuration to an expanded configuration, and wherein the stent is beveled at an edge and/or curved along the longitudinal axis for placement at the anastomosis; and
   c. Applying a sleeve comprising a biocompatible matrix material imbibed with a therapeutic agent to the external surface of the vascular structure containing the stent;
   wherein the method is performed in a single surgical procedure.

32. The method of claim 31, wherein the therapeutic agent comprises rapamycin or an analogue of rapamycin.

33. The method of claim 32, wherein the analogue of rapamycin is everolimus or zotarolimus.

34. The method of claim 32, wherein the rapamycin or an analogue of rapamycin is present in an amount of about 75 micrograms per $cm^2$.

35. A kit packaged for use in a single surgical procedure for preventing stenosis of a vascular structure that includes an anastomosis site, comprising:
   a. a drug-free stent for deployment within the vascular structure having a tubular body with a longitudinal axis and a circumferential diameter for placement at the anastomosis site; and
   b. a sleeve comprising a biocompatible matrix material imbibed with a therapeutic agent for placement on the external surface of the vascular structure containing the stent.

36. The kit of claim 35, wherein the therapeutic agent is selected from the group consisting of rapamycin, everolimus, zotarolimus, or other analogue of rapamycin.

37. The kit of claim 36, wherein the stent is curved along the longitudinal axis.

38. The kit of claim 36, wherein the rapamycin or an analogue of rapamycin is present in an amount of about 75 micrograms per $cm^2$.

39. A method for preventing stenosis in an AV fistula, comprising the following steps performed in a single surgical procedure:
   a. creating the AV fistula by joining a vein to an artery;
   b. deploying a drug-free stent at the anastomosis and the adjacent vein and/or artery, wherein the stent comprises a structure defining an essentially tubular body with a longitudinal axis and a circumferential diameter, the structure being expandable from a contracted configuration to an expanded configuration; and
   c. applying locally and externally to the anastomosis and adjacent vein and/or artery containing the stent an effective amount of rapamycin or everolimus or zotarolimus or other analogue of rapamycin via a biocompatible matrix material that carries the rapamycin or everolimus or zotarolimus or other analogue of rapamycin.

40. The method of claim 39, wherein the stent is beveled at an edge for placement at the anastomosis.

41. The method of claim 39, wherein the stent is curved along the longitudinal axis for placement at the anastomosis.

42. The method of claim 39, wherein the rapamycin or analogue of rapamycin is present in an amount of about 75 micrograms per $cm^2$.

43. The kit of claim 35, wherein the stent is partially or completely covered by a polymer or fabric.

44. The kit of claim 43, wherein the cover is PTFE.

45. The kit of claim 35, wherein the stent is a self-expanding or a balloon expandable stent.

46. The kit of claim 35, wherein the stent is beveled, flared or trumpeted.

47. The kit of claim 46, wherein the stent is beveled.

* * * * *